US010598914B2

(12) United States Patent
Siegel et al.

(10) Patent No.: US 10,598,914 B2
(45) Date of Patent: Mar. 24, 2020

(54) ENHANCEMENT OF VIDEO-RATE FLUORESCENCE IMAGERY COLLECTED IN THE SECOND NEAR-INFRARED OPTICAL WINDOW

(71) Applicant: MASSACHUSETTS INSTITUTE OF TECHNOLOGY, Cambridge, MA (US)

(72) Inventors: Andrew M. Siegel, Cambridge, MA (US); Nandini Rajan, Cambridge, MA (US); Angela M. Belcher, Cambridge, MA (US); Neelkanth M. Bardhan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 200 days.

(21) Appl. No.: 15/209,571

(22) Filed: Jul. 13, 2016

(65) Prior Publication Data

US 2017/0017069 A1    Jan. 19, 2017

Related U.S. Application Data

(60) Provisional application No. 62/192,233, filed on Jul. 14, 2015.

(51) Int. Cl.
*G02B 21/16* (2006.01)
*G01J 3/02* (2006.01)
(Continued)

(52) U.S. Cl.
CPC ............ *G02B 21/16* (2013.01); *A61B 5/0071* (2013.01); *A61B 5/0075* (2013.01); *G01J 3/0208* (2013.01);
(Continued)

(58) Field of Classification Search
CPC ................ A61B 5/0071; A61B 5/0075; G02B 21/0012; G02B 21/06; G02B 21/16;
(Continued)

(56) References Cited

U.S. PATENT DOCUMENTS 9,775,499 B2 *  10/2017  Scott ...................... A61B 1/043
2009/0268010 A1 *  10/2009  Zhao .................. A61B 1/00009
348/45

(Continued)

FOREIGN PATENT DOCUMENTS

EP          2698100 A1    2/2014

OTHER PUBLICATIONS

Chen, et al., Single Camera Imaging System for Color and Near-Infrared Fluorescence Image Guided Surgery, Biomedical Optics Express, 2014, 5(8):2791-2797.
(Continued)

*Primary Examiner* — Brian P Yenke
*Assistant Examiner* — Sean N. Haiem
(74) *Attorney, Agent, or Firm* — Quarles & Brady LLP; Yakov Sidorin

(57) ABSTRACT

System and method configured to operate under conditions when the object being imaged destroys or negates the information which otherwise allows the user to take advantage of optical parallax, configured to elicit luminescence from the same targets in the object as a result of irradiation of these targets with pump light at different, respectively corresponding wavelengths, and acquire optical data from so-illuminated targets through the very same optical path to image the object at different wavelengths. One embodiment enables acquisition, by the same optical detector and from the same object, of imaging data that includes a reflectance image and multiple fluorescence-based images caused by light at different wavelengths, to assess difference in depths of locations of targets within the object.

18 Claims, 29 Drawing Sheets

(51) Int. Cl.
| | |
|---|---|
| G01J 3/10 | (2006.01) |
| G01J 3/28 | (2006.01) |
| G01J 3/44 | (2006.01) |
| A61B 5/00 | (2006.01) |
| G01N 21/64 | (2006.01) |
| G02B 21/00 | (2006.01) |
| G02B 21/06 | (2006.01) |

(52) U.S. Cl.
CPC ............ *G01J 3/0248* (2013.01); *G01J 3/0264* (2013.01); *G01J 3/10* (2013.01); *G01J 3/108* (2013.01); *G01J 3/2823* (2013.01); *G01J 3/4406* (2013.01); *G01N 21/6456* (2013.01); *G02B 21/0012* (2013.01); *G02B 21/06* (2013.01); *G01J 2003/104* (2013.01); *G01J 2003/106* (2013.01)

(58) Field of Classification Search
CPC .......... G01J 3/0248; G01J 3/0264; G01J 3/10; G01J 3/108; G01J 3/2823; G01J 3/4406; G01J 3/0208; G01N 21/6456
USPC .............. 348/79, 45, 65; 600/317, 473, 431; 356/51; 424/9.6
See application file for complete search history.

(56) References Cited

U.S. PATENT DOCUMENTS

| | | | | |
|---|---|---|---|---|
| 2011/0063427 | A1* | 3/2011 | Fengler | A61B 1/00186 348/65 |
| 2013/0003044 | A1* | 1/2013 | Maier | G01J 3/44 356/51 |
| 2013/0230464 | A1* | 9/2013 | Yi | A61K 49/0056 424/9.6 |
| 2014/0171764 | A1* | 6/2014 | Kim | A61B 5/0071 600/317 |
| 2014/0221844 | A1* | 8/2014 | Crane | A61B 5/0059 600/473 |
| 2015/0182118 | A1* | 7/2015 | Bradbury | A61B 1/043 600/431 |
| 2015/0297086 | A1* | 10/2015 | Hong | G01N 21/6428 600/431 |
| 2016/0287081 | A1* | 10/2016 | Yang | A61B 90/361 |
| 2017/0014029 | A1* | 1/2017 | Azizian | A61B 5/7405 |

OTHER PUBLICATIONS

Chi, et al., Intraoperative Imaging-Guided Cancer Surgery: From Current Fluorescence Molecular Imaging Methods to Future Multi-Modality Imaging Technology, Theranostics, 2014, 4(11):1072-1084.

Frangioni, In Vivo Near-Infrared Fluorescence Imaging, Current Opinion in Chemical Biology, 2003, 7:626-634.

Gray, et al., Dual-mode Laparoscopic Fluorescence Image-Guided Surgery Using a Single Camera, Biomedical Optics Express, 2012, 3(8):1880-1890.

Hong, et al., Multifunctional In Vivo Vascular Imaging Using Near-Infrared II Fluorescence, Nature Medicine, 2012, 18:1841-1846 [Abstract Only].

Lee, et al., Fluorescence-Enhanced Absorption Imaging Using Frequency-Domain Photon Migration: Tolerance to Measurement Error, Journal of Biomedical Optics, 2001, 6(1):58-67.

Liu, et al., In Vivo Biodistribution and Highly Efficient Tumour Targeting of Carbon Nanotubes in Mice, Nature Nanotechnology, 2007, 2:47-52.

Robinson, et al., High Performance In Vivo Near-IR (>1 um) Imaging and Photothermal Cancer Therapy with Carbon Nanotubes, Nano Research, 2010, 3(11):779-793.

Robinson, et al., In-Vivo Fluorescence Imaging in the NIR-II with Long Circulating Carbon Nanotubes Capable of Ultra-High Tumor Uptake, J. Am. Chem Soc., 2012, 134(25):10664-10669.

Sevick-Muraca, Translation of Near-Infrared Fluorescence Imaging Technologies: Emerging Clinical Applications, Annual Review of Medicine, 2012, 63:217-231 [Abstract Only].

Stummer, et al., Fluorescence-Guided Surgery with 5-aminolevulinic Acid for Resection of Malignant Glioma: A Randomised Controlled Multicentre Phase III Trial, Lancet Oncology, 2006, 7:392-401.

Takahashi, et al., SPY(TM): An Innovative Intra-Operative Imaging System to Evaluate Graft Patency During Off-Pump Coronary Artery Bypass Grafting, Interactive CardioVascular and Thoracic Surgery, 2004, 3:479-483.

Thirion, Image Matching as a Diffusion Process: An Analogy with Maxwell's Demons, Medical Image Analysis, 1998, 2(3):243-260.

Troyan, et al., The FLARE(TM) Intraoperative Near-Infrared Fluorescence Imaging System: A First-in-Human Clinical Trial in Breast Cancer Sentinel Lymph Node Mapping, Ann. Surg. Oncol., 2009, 16(10):2943-2952.

Van Dam, et al., Intraoperative Tumor-Specific Fluorescence Imaging in Ovarian Cancer by Folate Receptor-a Targeting: First In-Human Results, Nature Medicine, 2011, 17(10):1315-1319.

Venugopal, et al., Design and Characterization of an Optimized Simultaneous Color and Near-Infrared Fluorescence Rigid Endoscopic Imaging System, Journal of Biomedical Optics, 2013, 18(12):126018-1 thru 126018-10.

Zhu, et al., Dual-Mode Optical Imaging System for Fluorescence Image-Guided Surgery, Optics Letters, 2014, 39(13):3830-3832.

Fluoptics, Fluobeam for In Vivo Fluorescence Imaging, http://www.fluoptics.com/fluoptics_Fluorescence_Imaging_System.php, Copyright 2015 Fluoptics.

Pulsion Medical Systems, PDE—Photodynamic Eye: Tissue Perfusion Gets Visible!, http://www.pulsion.com/international-english/perfusion/pde/, Copyright 2015 Pulsion Medical Systems SE.

PCT International Search Report and Written Opinion, PCT/US2016/042209, dated Dec. 20, 2016.

* cited by examiner

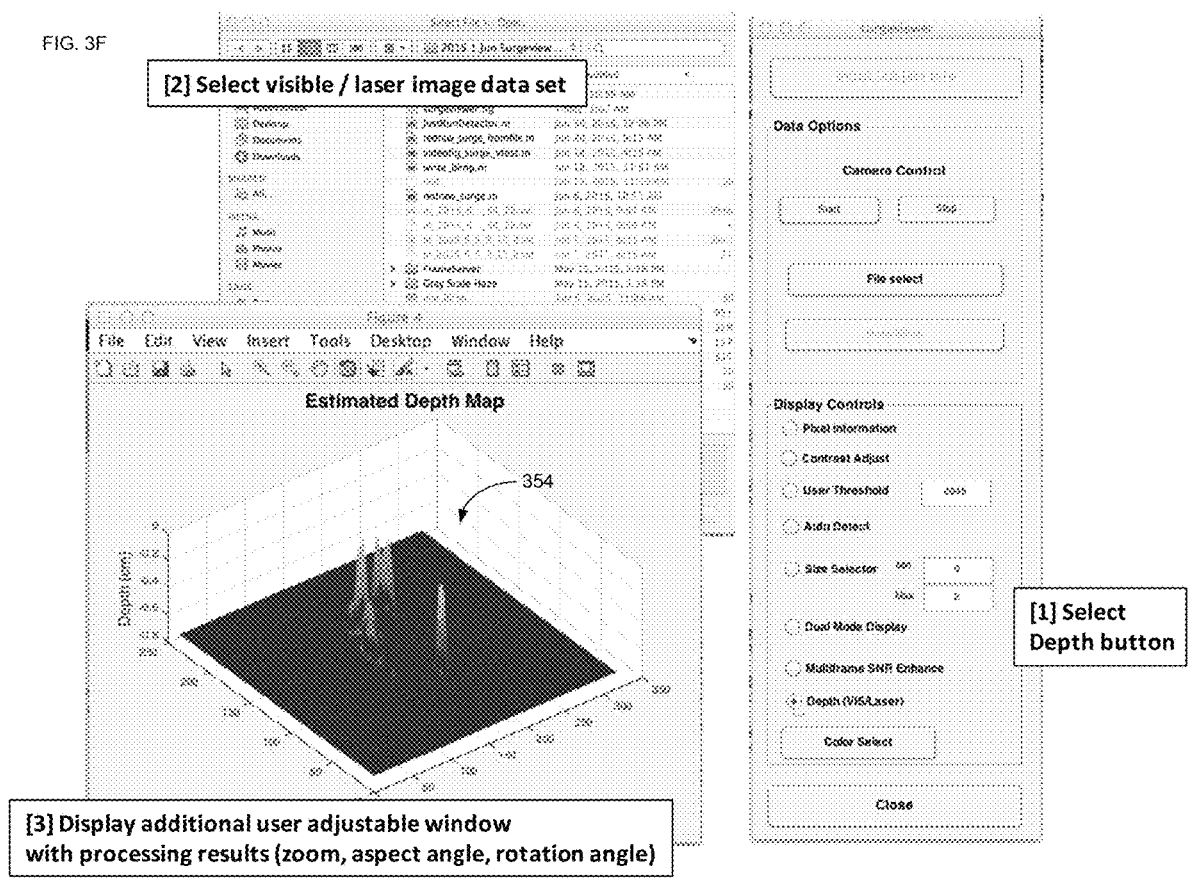

```
% Multi-frame Non-rigid registration and frame addition to generate single frame increase SNR and
% contrast image as data product % Clean workspace
clc; clear all;
close all;

% Compile the mex files required to run the demon nonrigid motion registration algorithm
compile_c_files % Read in sequence of images for processing
% If using bimg_inband to enhance bimg_laser data, the assumption is acquisition is
% interleaved with each frame rate equal to half of frame rate of camera
% (15 fps for 30 fps camera system), bimg_inband video data is used to
% derive motion compensation for non-rigid body motion which is then
% applied to the interleaved bimg_laser data (using the derived Tx, Ty from bimg_inband
% as defined in code below).
% The resulting compensated bimg_laser only data is displayed by selecting the dynamic range display
% associated with laser-only image data (approximate pixel value range -
% 2000 - 2200, laser power setting 3, derived from user-defined thresholds
% over several dozens of animal data collects % For combined in-band + laser source illumination, we use bimg_combined
% for non-rigid body registration and co-adding with final product of laser
% only image displayed by dynamic range display associated with laser-only
% image data (approximate pixel value range from measurements - 2000-2200,
% laser power setting 3, derived from user-defined thresholds over several
% dozens of animal data collects. This is shown implemented in code below.

datadir = '/Users/na16046/Desktop/04-09-15 Mouse Data';
load data
%These first two sets are used for interleaved in-band +
% laser source illumination
% bimg = bimg_inband;
%bimg2 = bimg_laser;
```

FIG. 4G

```
%Using the data from simultaneous operation of in-band and laser pump
%sources
bimg = bimg_combined; % This data is comprised of a combined HIGH CONTRAST in-band
                     % REFLECTANCE image (for enhanced nonrigid registration
                     % accuracy) AND the diffuse (lower contrast) fluorescence
                     % image from simultaneous illumination from in-band
                     % and laser pump source I1 = bimg.imgs{1};
S = I1; % define first frame of video sequence (multiple frame set) as the reference image (frame)
alpha=2.5; % weighting term

[nr,nc] = size(I1);
bimgMov{1}.data = I1; % Motion compensated image. first image is just the reference image.

%BEGIN DEMON REGISTRATION
for ii=2:length(bimg.imgs), % register using non-rigid body registration each image
                            % frame to reference. in this case,
                            % length(bimg.imgs) = 200 frames.

% Set moving image I2 to next frame in video sequence
    M= bimg.imgs{ii};
    I2 = M;

% Alpha (noise) constant

% velocity field smoothing kernel
    Hsmooth=fspecial('gaussian',[60 60],10);

% The transformation fields
    Tx=zeros(size(M)); Ty=zeros(size(M));

% Calculate image gradients from reference image
    [Sy,Sx] = gradient(double(S));

for itt=1:50
        % Difference image between moving and static image
        Idiff=double(M-S);
```

FIG. 4H

```
%==========================================================
% Extended demon force. With forces from the gradients from both
% moving as well as static image. (Cachier 1999, He Wang 2005)
[My,Mx] = gradient(double(M));
Ux = -Idiff .* ((Sx./((Sx.^2+Sy.^2)+alpha^2*Idiff.^2))+(Mx./((Mx.^2+My.^2)+alpha^2*Idiff.^2)));
Uy = -Idiff .* ((Sy./((Sx.^2+Sy.^2)+alpha^2*Idiff.^2))+(My./((Mx.^2+My.^2)+alpha^2*Idiff.^2)));

% When divided by zero
Ux(isnan(Ux))=0; Uy(isnan(Uy))=0;

% Smooth the transformation field
Uxs=3*imfilter(Ux,Hsmooth);
Uys=3*imfilter(Uy,Hsmooth);

% Add the new transformation field to the total transformation field.
Tx=Tx+Uxs;
Ty=Ty+Uys;

%Move pixels using the transformation field as motion direction
%field for each pixel
M=movepixels(I2,Tx,Ty); % Also from He Wang 2005
%==========================================================
end
bimgMov{ii}.data = M; % This is the non-rigid registered frame to reference image
clear M Tx Ty Sx Sy end
```

FIG. 4i

% END DEMON REGISTRATION

% Use all registered frames (bimgMov) now by adding up all frames
% (spatially coherent integration) to increase image contrast and SNR.
sumval = zeros(size(bimgMov{1}.data));
for ii=1:length(bimgMov),
    sumval = sumval + double(bimgMov{ii}.data);
end
sumval = sumval/length(bimgMov);

% Display enhanced image using appropriate dynamic range to display only
% laser image or entire range to display the reflectance in-band reference
% image figure;imagesc(sumval);axis image; colormap gray;
caxis([2000 2200]);

% Alternately user defined thresholds figure;imagesc(sumval);axis image; colormap gray;
imcontrast; % matlab defined utility

FIG. 4J

```
load data;

addpath('/Users/na16046/Desktop/SurgeViewer/PRACTICE VER 2 WITH FRAMESERVER');

% load up a visible and a laser induced fluorescence data set that are
% separated by no more than a single frame time interval (1/30fps for our
% camera system)

visible = bvisible.imgs{1};
laser = blaser.imgs{1};

% run the tumor detection algorithm runAdvancedDetector on both sets of data
% 0,0 indicates that all tumors are selected with no user-defined size ranges
[curdetecthi_vis, curdetectlow_vis] = runAdvancedDetector(visible, 0, 0);
[curdetecthi_las, curdetect_low_las] = runAdvancedDetector(laser, 0, 0);

% run a morphological filter to clean up detections due to bad pixels in camera focal plane
% array
curdetectlow_vis_clean = bwmorph(curdetectlow_vis,'clean');
curdetectlow_las_clean = bwmorph(curdetectlow_las,'clean');

% identify shallow tumors as those that are detected in visible data
shallowtumors = curdetectlow_vis_clean;
shallowtumors_realvalue = shallowtumors .* double(visible);

% find the overlap with the laser induced fluorescence image - neat trick
% is to subtract the vis detection from laser. Cluster the data sets and label.
% Use the euler number for each cluster to determine number of holes. Anything
% with euler number <1 is shallow tumors detectable by both VIS and laser,
% everything else are deeper tumors detectable only by laser shallowtumors_inv = abs(1-shallowtumors);
othertumors = shallowtumors_inv .* curdetectlow_las_clean;
[L,num] = bwlabel(othertumors);
s = regionprops(L,'EulerNumber');
eulernumbers = cat(1,s.EulerNumber);
[ind_euler_overlap] = find(eulernumbers< 1); % these are the ones we found in the visible only
```

FIG. 6A

```
newshallowtumors = zeros(size(shallowtumors));

for index= 1:length(ind_euler_overlap),
    [ind_binary] = find(L == ind_euler_overlap(index));
    newshallowtumors(ind_binary) = 1;
    clear ind_binary;
end
newshallowtumors = newshallowtumors + shallowtumors;
newshallowtumors_real = newshallowtumors .* double(laser);

%2 way attenuation is modeled as exp(-2*alpha_fluorescence/depth);
%Make assumption that fluorphore yield is same per pixel (assume flat
%tumor model) and that the values at surface are at 1 mm penetration
%depth. [VIS light absorption coefficient of Water is 0.1 cm-1.]

alpha_fluorescence = 1 ; %(1/cm) ;

% pull out image components corresponding to deeper tumors
newshallowtumors_inv = abs(1-newshallowtumors);

deepertumors = newshallowtumors_inv .* curdetect_low_las_clean;
deepertumors_realvalue = deepertumors .* double(laser);
[L2,num] = bwlabel(deepertumors);
s = regionprops(L2,deepertumors_realvalue,'MaxIntensity');
s_peak = cat(1,s.MaxIntensity);

%set peak count value in VIS image as a initial emission value at .001 cm
max_intensity_nosaturation = max(newshallowtumors_real(:));

% Generate depth attenuation model:

%f(d) = fo (1/d)exp(-2d/lambda) where lambda = alpha_fluorescence = 1;
%f(d) = fo * q(d)

d = 0.001:0.01:3; % up to 3 cm
%q = exp(-2d);
q = exp(-2*d/alpha_fluorescence); % two way path
```

FIG. 6B

```
% estimation depth for laser image
[x,y] = max(newshallowtumors_real(:));
[II,JJ] = find(curdetectlow_las_clean>0);
D2 = zeros(size(newshallowtumors));
grayscaleimage = curdetectlow_las_clean .* double(laser);
for ii=1:length(II)
    Ival = grayscaleimage(II(ii),JJ(ii));
    ratio = Ival/max_intensity_nosaturation;
    y = abs(q - ratio);
    [val,indexer] = min(y);
    D2(II(ii), JJ(ii)) = -d(indexer);
end D2new = D2(5:end,5:end); % get rid of boundaries
minvalues = min(D2new(:));
[ind] = find(D2new==0);
D2new(ind) = minvalues - 0.001; % make sure that peak value is set to the shallowest subsurface depth % Display tumor depth below exposed surface (at 0)
figure; mesh(D2new);
```

FIG. 6C

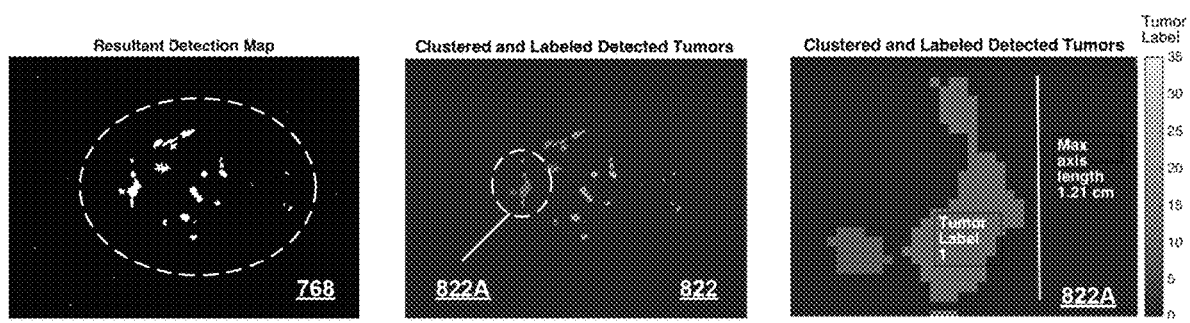
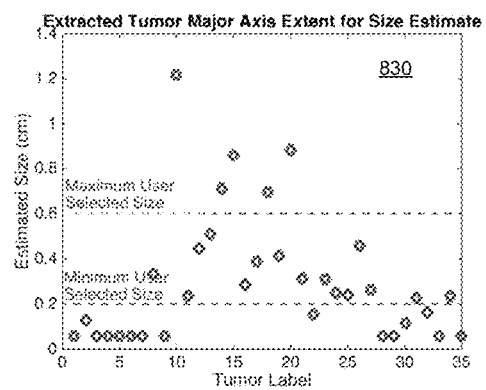
FIG. 8B

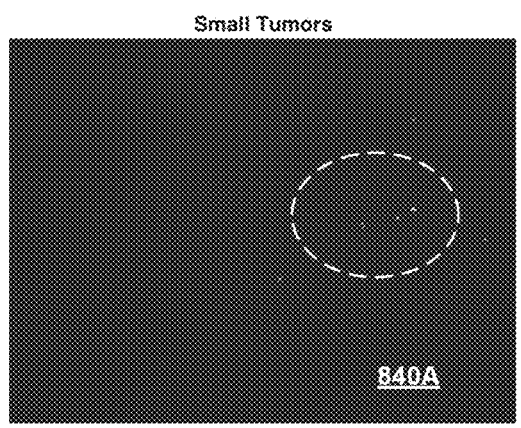
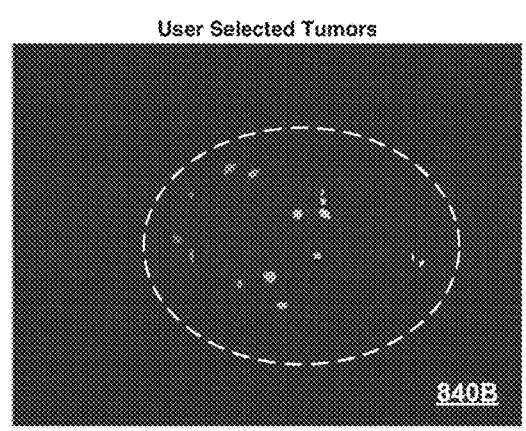
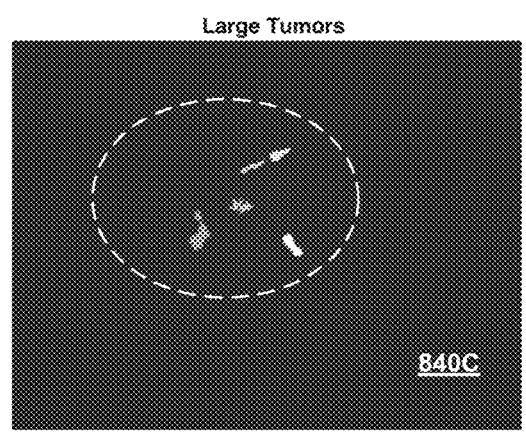
FIG. 8C

```
function [curdetecthi, curdetectlow, L_operable, L_small, L_large, relative_signal] = ...
    runAdvancedDetector(inputimage, tumor_size_lower_limit, tumor_size_upper_limit)
%================================================================
% INPUTS:
% inputimage : single image frame from camera
% tumor_size_lower_limit: linear extent (in pixels) of smallest tumor size
% (in mm)
% tumor_size_upper_limit: linear extent (in pixels) of largest tumor size
% (in mm)
%
% OUTPUTS:
% curdetecthi: high confidence detections
% curdetectlow: low confidence detections
% Display of operable tumor sizes
%================================================================

Scale_factor = .05 ;% (cm) 1 pixel = 0.5 mm @ 18" height, pixel resolution - a function of optics/camera/position FilterSizes = [32 16 8 4]; % filter Sizes determined via range of measured tumor sizes (in pixel space)
    % from several several dozen animal studies.
    % Each filter size corresponds to a length scale
    % associated with the background clutter (not
    % tumor).

% The data is filtered with each filter of FilterSizes (a gaussian filter, for example
% defined below). This is the background model at this scale. The background model at a fixed scale is
% then subtracted from the original data to get a background-subtracted
% data set. What remains should be the background subtracted tumor data in
% shot + read noise alone at different background scales.

% The simplest filter class was selected - gaussian
% This filter can also be replaced by another base - square window,
% lorentzian, a wavelet base function such as the "mexican hat" wavelet
```

FIG. 9A

```
for ii=1:length(FilterSizes)
    curfilter= fspecial('gaussian',FilterSizes(ii)*3, FilterSizes(ii));
    In_med{ii} = imfilter(inputimage, curfilter, 'same');
    dat_sub{ii} = double(inputimage) - double(In_med{ii});
end % Since the size of tumors and background scales are unknown in advance,
% all scale background subtracted images are utilized to generate a final
% tumor detection mask - a binary mask with a value 1 for pixels associated
% to positive tumor detection and 0 for pixels associated with background.

Total = zeros(size(inputimage), 'double');

for ii=1:length(FilterSizes)
    Total = Total + double(dat_sub{ii});
end

Total = Total/length(FilterSizes);

% Here, we just calculate global statistics for SNR calculations for real-time tumor
% detection (@ 30 fps).
% For a slight delay (2 frame delay  resulting in 15 fps detection rate),
% local statistics can be determined:
% Fix WinSize = max(FilterSizes)
% For each pixel location (x,y)
% Define data = Total(x-WinSize:x+WinSize, y-WinSize:y+WinSize);
% meanval(x,y) = mean(data(:));
% stdval(x,y) = std(data(:));
meanval = mean(Total(:));
stdval = std(Total(:));

val = (Total - meanval)./stdval; % this gives a local linear signal to noise ratio curdetectlow = zeros(size(Total));
curdetecthi = zeros(size(Total));

maxval = max(inputimage(:));
```

FIG. 9B

```
% Define thresholds above which you declare a detection; SNR > Threshold
% The two thresholds correspond to a low confidence and a high confidence
% detect based off of data analysis across several dozen animal experiment
% data sets
Threshold2 = 3.5; % low confidence - higher probability of false alarm rates
Threshold3 = 5; % higher confidence - increased probability for missed detection rates

[ind2] = find(val>Threshold2);
[ind3] = find(val>Threshold3);

% Resultant binary detection maps
curdetectlow(ind2) = .5;
curdetecthi(ind3) = 1;

%==================================================
% Filter by user defined tumor size and display desired operable size

[L,num] = bwlabel(curdetectlow); % cluster and label binary detection data s = regionprops(L,'MajorAxisLength');
tumor_majoraxis_pixels = cat(1,s.MajorAxisLength);
tumor_majoraxis_mm = tumor_majoraxis_pixels * Scale_factor;

[ind_justright] = find(tumor_majoraxis_mm > tumor_size_lower_limit & tumor_majoraxis_mm < tumor_size_upper_limit);
[ind_smaller] = find(tumor_majoraxis_mm <= tumor_size_lower_limit);
[ind_larger] = find(tumor_majoraxis_mm >= tumor_size_upper_limit);

L_operable = zeros(size(L));
L_small = zeros(size(L));
L_large = zeros(size(L));

% Get operable tumors
for ii=1:length(ind_justright),
    [indval] = find(L == ind_justright(ii));
    L_operable(indval) = L(indval);
    clear ind_val;
end
```

FIG. 9C

ENHANCEMENT OF VIDEO-RATE FLUORESCENCE IMAGERY COLLECTED IN THE SECOND NEAR-INFRARED OPTICAL WINDOW

CROSS-REFERENCE TO RELATED APPLICATIONS

This patent application claims priority from and benefit of the U.S. Provisional Patent Application Ser. No. 62/192,233 filed on Jul. 14, 2015, the disclosure of which is incorporated herein by reference.

STATEMENT REGARDING FEDERALLY SPONSORED RESEARCH

This invention was made with government support under Contract No. FA8721-05-C-0002 awarded by the U.S. Air Force. The government has certain rights in the invention.

TECHNICAL FIELD

The present application relates to imaging methodologies and, in particular, to system(s) and method(s) for image transformation to visually enhance characteristics acquired in the second near-IR spectral region.

BACKGROUND

NIR fluorescence-based imaging finds various applications in areas ranging from assessment of neuronal activity to sentinel lymph node identification and improved tumor detection and delineation. Because of the potential for high-sensitivity tumor detection in real-time, interest of the scientific community has been recently directed to fluorescence imaging systems operating mostly in the first NIR window (or NIR-1) for image-guided uses. Systems leveraging fluorescent dyes such Indocyanine green (ICG) and methylene blue (MB) include a FLARE™ system, a Fluobeam system, SPY, FDPM, and a Photodynamic Eye system, for example. Most of these utilize either a single image sensor (typically, a CCD) to capture visible (a reference image) and fluorescence images sequentially, or multiple cameras to form images in different spectral ranges simultaneously or sequentially.

For imaging systems that produce multiple images with the use of multiple cameras and/or sequential image acquisition, subsequent image registration is required (see Zhu, N. et al, "Dual Mode optical imaging system for fluorescence image-guided surgery", Opt. Lett. 39(13); 3830-3932, 2014). To properly coordinate different spatial parameters of the multiple images, such image processing must take into account changes in angular coordinate(s), potential relative motion between the system and the subject, or both. Other types of imagers include imaging lenses that are configured for measurements of different emission spectra in absence of the visible reference window (Gray, D. C. et al., "Dual-mode laparoscopic fluorescence image-guided surgery using a single camera", Biomed. Opt. Express, 3(8):1880-1890, 2012) and/or specialized CMOS sensors that can collect light via red-green-blue channel(s) (RGB) as well as a single channel in NIR-1 (Chen. Z et al., "Single camera imaging system for color and near-infrared fluorescence image guided surgery", Biomed. Opt. Express, 5(8): 2791-2797, 2014).

Fluorescent imaging systems and methodologies possess well-recognized shortcomings limiting the operational capabilities of these systems. For example, some systems providing fused visible/fluorescence imagery with the use of a single, the only, image sensor, employ silicon-based detection units the sensitivity of which is limited to the visible and/or NIR-I spectral bands, in which case expensive spectral filters are additionally required to maintain the spectral purity of the passbands of the light source(s) and the detector (due to the fact that the spectral separation between the spectral band of the source of light and spectral band(s) within which the optical detection is carried out is very narrow). On the other hand, images acquired with the systems that employ two or more separate detectors to capture the radiation in the visible, NIR-I, and/or NIR-II spectral bands must be fused to create a combined image. To effectuate quality image fusion, such imaging systems must maintain precise optical alignment and positioning during the imaging procedure, which adversely impacts their size, weight, and cost.

Accordingly, there remains a need for a system and methodology overcoming deficiencies of the related art and enabling real-time detection and assessment of distribution of targets in object, both those located at or near the surface and those embedded within the object (such as, in a specific non-limiting case, the distribution of tumors in a tissue sample) for imaging of those targets.

SUMMARY

Embodiment of the invention provides a fluorescence-based imaging system that includes (i) an optical system containing an optical train of components and an optical detector characterized by a spectral band of operation and disposed in optical communication with the optical train; (ii) first and second light sources configured to emit respectively-corresponding first light and second light at respectively-corresponding first and second wavelengths, such that the first light is received in direct reflection of light, that has been emitted by the first light source, from the object and the first fluorescent light includes fluorescence generated, at a first fluorescence wavelength, at a first portion of the object as a result of interaction of the object with the second light. Here, both the first wavelength and the first fluorescence wavelengths are within the spectral band of operation (which may be defined within the NIR-II spectral band). The first and second light sources are configured to operate in a time-multiplexed fashion or, alternatively, simultaneously, either automatically or under the external user control.

The imaging system may additionally include an auxiliary light source configured to emit light at an auxiliary wavelength and disposed in optical communication with the optical detector such that during imaging of the chosen object, while the second fluorescent light including fluorescence generated at the first fluorescence wavelength at a second portion of the object (as a result of interaction of said second portion with the auxiliary light) is received by the optical detector. Here, the first and second portions of the object are separated from the optical detector by respectively-corresponding and different first and second distances, the first and second distances being different from one another, and the second fluorescent light is received by the optical detector along the same optical path through the same optical train.

An embodiment of the invention additionally provides a fluorescence-based imaging system comprising: (i) an optical system including an optical train of components and a single optical detector in optical communication with the optical train, the single optical detector having a spectral band of operation, and (ii) first and second light sources configured to emit respectively-corresponding first light and second light at respectively-corresponding first and second wavelengths. Here, the first light is received in direct reflection from the object, while the first fluorescent light includes fluorescence generated, at a first fluorescence wavelength, at a first portion of the object as a result of interaction of the object with the second light. Both the first wavelength and the first fluorescence wavelengths are within the spectral band of operation. The first and second wavelengths are defined such that, during imaging of a chosen object, the first light and first fluorescent light are received by the single optical detector along the same optical path through said optical train (the spectral band of which may be defined within the NIR-II spectral region). The imaging system may additionally include an auxiliary light source configured to emit light at an auxiliary wavelength and disposed in optical communication with the optical detector such that, during imaging of the chosen object, second fluorescent light including fluorescence generated (at the first fluorescence wavelength) at a second portion of the object as a result of interaction of the second portion with the auxiliary light. Here, the first and second portions of the object are separated from the optical detector by respectively-corresponding and different from one another first and second distances, and the second fluorescent light is received by the optical detector along the same optical path through said optical train.

Embodiments of the invention additionally provide a method for imaging an object, that includes the step of (i) acquiring, with an optical imaging system that having an optical detector with a spectral band of operation, first light and second fluorescent light from the object. Here, the first light has a first wavelength and is generated by a first light source within the spectral band of operation and reflected by the object towards the optical detector; the first fluorescent light has a first fluorescent wavelength and is generated by a marker, contained at the object, in response to irradiation of such marker with light from a second light source, and the first fluorescent wavelength is within a second near-infrared (NIR-II) spectral region. The method additionally includes the step of (ii) assessing a value representing a difference between a first separation distance and a second separation distance, the first separation distance representing a separation between a first portion of the object and the optical detector along an axis of the optical system, the second separation distance representing a separation distance between a second portions of the object and the optical detector along the axis. Here, the first portion is associated with direct reflection of the first light, the second portion is associated with generation of the first fluorescent light and contains such marker.

The marker includes a single-walled carbon nanotube (or another fluorophore which emits in the NIR-II spectral band), while the step of acquiring may manifest in collecting the first light and the first fluorescent light through the optical imaging system along the same optical path and, optionally, be devoid of mutual repositioning of the optical detector and the object. The first wavelength may be defined within the NIR-II spectral band, in which case both the reflectance and fluorescence images are acquired "in-band". The method may additionally include the steps of (iii) irradiating the object with auxiliary light; (iv) acquiring, with the optical imaging system, third light from a third portion of the object (where the third portion is separated from the optical detector by a third distance along the axis such that the second and third distances are not equal to one another). Here, third light includes fluorescence generated, at the first fluorescence wavelength, at the third portion of the object as a result of interaction of said second portion with the auxiliary light. Additionally or in the alternative, the step of irradiating may include irradiating of the object with auxiliary light generated by the same second source.

BRIEF DESCRIPTION OF THE DRAWINGS

The invention will be more fully understood by referring to the following Detailed Description of Specific Embodiments in conjunction with the not-to scale Drawings, of which:

FIGS. 3A, 3B, 3C, 3D, 3E, and 3F illustrate examples of operation of an automated interface showing tumor detection and morphology displays generated with the use of program code(s) configured according to an embodiment of the invention. FIG. 3A: a Data Viewer with a GUI 300. FIG. 3B: an illustration of image-overlap produced with the use of detection modality utilizing a multi-scale detection, according to the invention. FIG. 3C illustrates multiple adjustable windows, produced as part of the operation of the interface 300, providing visualization of results of imaging produced by analogy with that of FIG. 3B but additionally adjusted according to the target size selector 330B. FIG. 3D presents elements of the interface and menu of an embodiment of the invention representing multi-frame signal-to-noise ratio. FIG. 3E illustrates, in part, a dual-mode display screenshot selected for visualization of both reflectance and fluorescence images, and/or of either image displayed individually, through a user adjustable dynamic range display, as acquired with an embodiment of the invention. FIG. 3F illustrates an estimated depth map generated by an embodiment of the invention when images are acquired sequentially with the use of a light source producing light that penetrates the object at a small depth (images of shallow-localized targets) and a light source producing light penetrating the object at a larger depth (deeper localized target).

FIG. 4A: an overall image of the object acquired in light 130 containing the combination of the in-band light reflected by the object and fluorescence caused by irradiation of the object with light beams 124A and 128A of the embodiment of FIG. 1A. FIG. 4B: an image of FIG. 4A enhanced according to an embodiment of the invention to emphasize the contribution of fluorescence. FIG. 4C: an image of the object produced by collecting only the fluorescence generated by the object in response to irradiation with beam 128A only, shown for comparison with FIG. 4B and evidencing the efficacy of the proposed methodology.

FIG. 4D is the processing flowchart itemizing processes of simultaneous acquisition of both an image in direct reflection of light from the object/target (a reflectance image) and an image formed in fluorescent light produced by the object/target in response to light absorbed therein (a fluorescent image), pipeline A and multi-frame processing pipeline B. FIG. 4E illustrates a single image frame representing a moving and deforming object containing a target irradiated with deeply penetrating light. FIG. 4F is the result of combining multiple image frames produced as a results of the pipeline B process of FIG. 4D to improve a signal-to-noise ratio in the image of the target.

FIGS. 4G, 4H, 4i, 4J aggregately illustrate program code for improving target signal-to-noise ratio according to the flowchart of FIG. 4D.

FIGS. 6A, 6B, 6C aggregately illustrate program code for recovery of approximate depth of a target according to the code of the flow-chart of FIG. 5A;

FIGS. 8B, 8C, 8D illustrate image frames utilized and/or produced at different steps of the process represented by FIG. 8A.

FIGS. 9A, 9B, 9C aggregately illustrate program code for detecting targets of varying sizes and subsequently displaying images of these targets categorized by size according to the flow charts of FIGS. 7A and 8A.

Figure 1A:
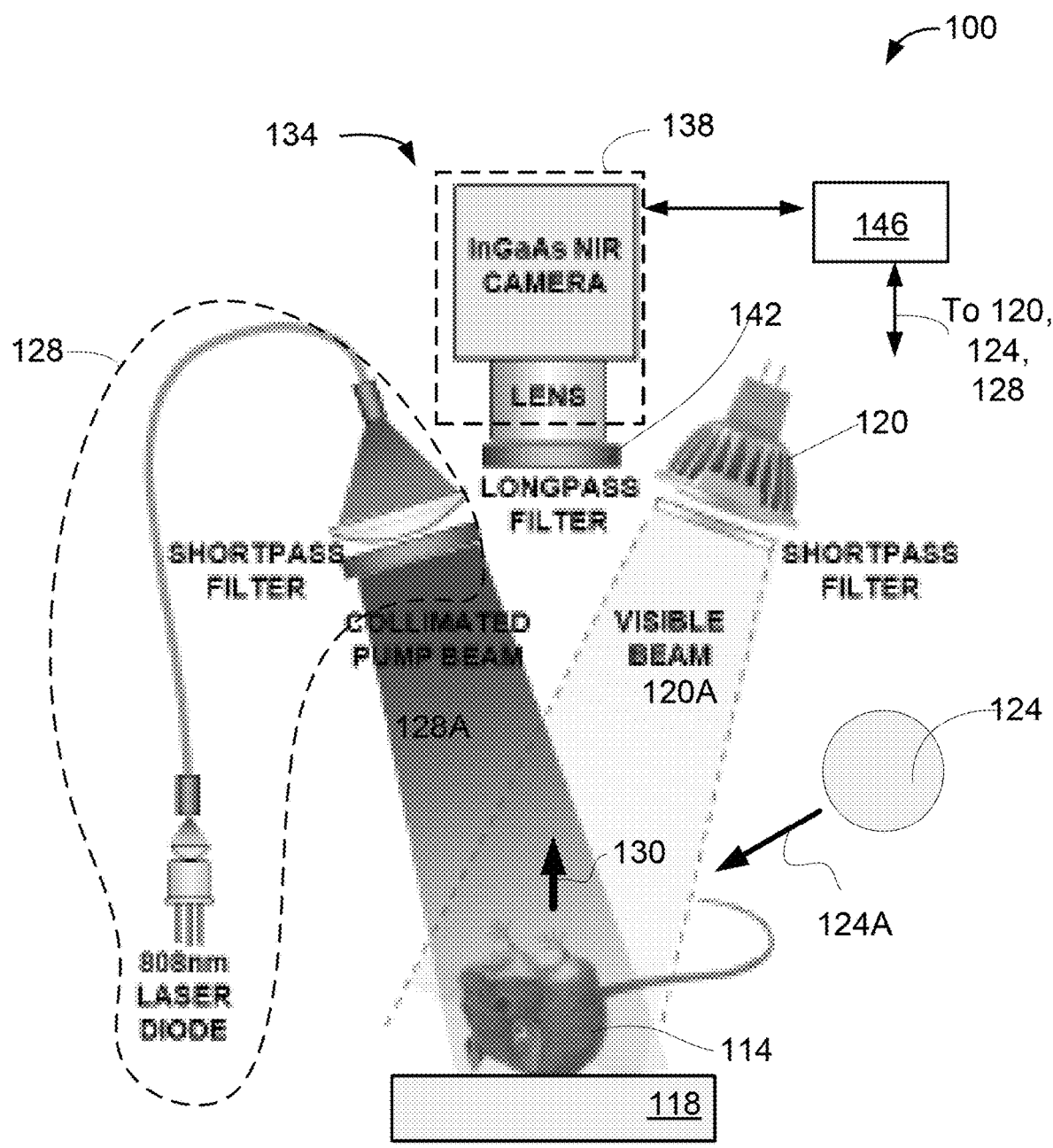
FIG. 1A is a schematic diagram of an embodiment of the system of the invention configured for NIR-II imaging of an object irradiated with light delivered from a combination of light sources one of which operates within the NIR-II band of spectral sensitivity of an optical detection sub-system of the embodiment.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of this disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented in this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

Furthermore, the described features, structures, or characteristics of the invention may be combined in any suitable manner in one or more embodiments. Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown. The invention as recited in claims appended to this disclosure is intended to be assessed in light of the disclosure as a whole.

In accordance with preferred embodiments of the present invention, intra-operative system employing visible (VIS) imaging and fluorescence imaging in the NIR-II band and related method(s) with the use of functionalized fluorescent probes. Embodiments of the invention utilize novel fluorophores configured to emit light in the NIR-II band (generally considered within the range of wavelengths from about 900 nm and about 2,000 nm, and for the purposes of the disclosure preferably from about 900 nm to about 1,400 nm), and provide the user with a real-time (or near real-time) augmented imagery (which, in the case of diagnostic imaging and/or surgical resection of tumors during the course of an intra-operative procedure, facilitates the enhancement of such resection). For the purposes of this disclosure and accompanying claims, a real-time performance of a system is understood as performance that is subject to operational deadlines from a given event to a system's response to that event. For example, a real-time extraction of optical data (such as irradiance or phase data) from an acquired optical image of an object may be one triggered by the user and executed simultaneously with and without interruption of an image acquisition procedure. In a specific case, real-time performance includes an image-processing delay that is comparable in duration with the time of acquisition of a single image frame (of about 30 msec, give or take 5 msec, for example), while near real-time performance includes a processing delay that is longer than the time of acquisition of two consecutive image frames but is still short enough to effectuate surgical guidance by screen imagery alone. As a related example, a real-time creation of the final image output from the system of the invention that is useful to the user in the context of image-guided surgical procedure is defined at the minimum video rate (of the NIR-II camera of the system of the invention) on the order of 1 Hz or greater.

Embodiments of the method of the invention leverage multiple image frames to enhance contrast and improve detection of targets associated with an object (in one specific example, used in this disclosure only for a specific illustration of the proposed methodology but, otherwise, not intended to limit the scope of the invention—the detection of micro-tumors or tumors embedded in a biological tissue and/or to aid the user such as a clinician, in the discussed specific example, in the study of pharmacokinetics and drug delivery).

Accordingly:

A problem of structural and operational complexity of existing fluorescence-based imaging systems and methods configured to operate under conditions when the object being imaged destroys or negates the information, which would otherwise allow the user to take advantage of optical parallax (and, therefore, negates the ability to differentiate between portions of or targets in the object located at different distances from an optical detector), is solved by providing a fluorescence-based imaging system and method (i) that are configured to elicit luminescence from the same targets on or in the object as a result of irradiation of these targets with pump light at different, respectively corresponding wavelengths, and (ii) that is configured to acquire optical data from so-illuminated portions or targets through the very same optical path and the very same train of optical components to image the object at different wavelengths, in contradistinction with imaging systems of related art. In particular, the proposed solution enables the acquisition, from the same object, of imaging data that includes of a first fluorescence-based image (caused by light at the first wavelength) and a second fluorescence-based image (caused by light at the second wavelength) from the same targets in the object and by the same optical detector. Light at the first and second wavelengths generating fluorescence from the same targets in the object is being absorbed and/or scattered by the object in different amounts, facilitating the determination of target depth without the presence of optical parallax.

A related problem of structural and operational complexity of existing fluorescence-based imaging systems and methods employing a multi-wavelength illumination of the object stems from the fact that wavelengths of such illumination are chosen to define light returned by the object to the optical detection system to have first and second wavelengths only one of which falls within the spectral band of a given optical detector while another is chosen to be outside of such band. This problem is solved by providing a fluorescence-based imaging system that is equipped, in stark contradistinction with any configuration of a system of related art, with first and second light sources which cause the object to produce an optical response at first and second wavelengths both of which fall within the spectral band of operation of the single, the only optical detector used in the imaging system. The sources are used to independently illuminate the object either simultaneously or in a time-multiplexed fashion. In particular, such configuration facilitates the acquisition, from the same object, of imaging data representing a direct reflection or scattering of light at the first wavelength and a fluorescence-based image acquired from light emitted by targets in the object, which can be either interleaved in time or received at the same time by the same optical detector.

An operational problem inherent to existing fluorescence-based imaging systems and methods configured to operate under conditions when the object has to be imaged in light elastically scattered by the object is solved by providing a fluorescence-based imaging system (i) that is equipped with judiciously-chosen multiple sources of light (independently illuminating such portions or targets either simultaneously or in a time-multiplexed fashion) and with a single, the only optical detector, and (ii) that is configured to acquire optical data from light reflected (elastically scattered) by the object and from fluorescent light emitted (inelastically scattered) by so-illuminated portions of, or targets within the object with the optical detector. In particular, as a result of such configuration, the use of the proposed imaging system for imaging of a portion of a biological tissue in light at wavelengths that are reflected, scattered, and absorbed by the tissue facilitates the use of the very same optical path and the very same train of optical components for imaging of the object at different wavelengths (including wavelengths reflected, scattered, and absorbed by the tissue in different amounts and wavelengths emitted by luminescence from targets in or on the tissue), in stark contradistinction with imaging systems of related art.

Yet another related problem, recognized in the art to be present in fluorescence-based imaging under conditions when the inherent fluorescence of the object is excessive in the range of wavelengths spanning from about 700 nm to about 950 nm is the limited ability to block the light used to generate fluorescence from being detected by the optical detector. At least in part, such problem is caused by the narrow Stokes shift associated with the fluorophores normally used during such imaging operation and by the finite spectral blocking limits of the optical filters. This problem is addressed by providing a fluorescence-based imaging system and method configured to utilize an optical detector sensitive at wavelengths longer than 950 nm and light sources emitting light at wavelengths shorter than 950 nm, aggregately with the use of fluorophores exhibiting large Stokes shifts and which fluoresce in a waveband between about 1000 nm and about 1800 nm, in contradistinction with imaging systems of related art. In a specific case, such a system and method is configured to use an optical detector sensitive in the range generally between about 950 nm and about 1800 nm and to employ fluorophores (in affinity with targets at the object) that exhibit Stokes shift(s) of around 600 nm. Optical sources operating at wavelengths around 808 nm excite fluorescence from targets that is detected by the optical detector, while light from the optical sources themselves and the inherent fluorescence (autofluorescence) emitted by the object are only weakly (if at all) detected by the optical detector that substantially lacks the spectral sensitivity at these wavelengths. In one example, positioning a spectral filter element that does not transmit light between 830 nm and 2000 nm (in a fashion equivalent to that of regular-grade filters) in front of the 808 nm optical source was shown to substantially improve contrast of the fluorescent imaging by blocking light emitted by the optical source at wavelengths longer than 830 nm according to an embodiment of the invention.

Another related problem of related art arises when a fluorescence-based imaging system and method are configured to operate at high image frame rates or under conditions when the object cannot be individually or exclusively illuminated by optical sources of varying intensity while imaging is carried out in light elastically scattered from the object surface. This problem is solved by providing a fluorescence-based imaging system which includes an optical detector (and, in a specific case, the single, the only optical detector) sensitive to light reflected by and emitted from the object and multiple optical sources with wavelengths chosen to create reflectance images of the object and fluorescence images of targets (within the object), in which the optical sources are illuminating the object and targets continuously such that both the reflected light and the fluorescent light emitted at the targets reach the optical detector at the same time. In a specific case, such a system is configured to generate both an image of the object generated by light elastically scattered from the object surface and an image of the object generated by fluorescent light emitted by targets within the object by adjusting the intensity of the optical sources. The intensity adjustment in this non-limiting example is tailored to ensure that the range of signals generated by the single, the only, optical sensor in response to only light reflected from the object never exceeds half-a-scale of the strength of light which would saturate the optical sensor from the object and that the range of a signal generated by the optical sensor in response to only fluorescent light from the targets always exceeds half-the-scale. In this example the fluorescent imagery at least partially saturates the optical sensor. At the same time, however, the reflected light signal in areas not saturated by fluorescence is still represented, which is the intent. Note that the intensity of both optical sources can, using electronic feedback control techniques, be automatically adjusted to accommodate changes in object and target brightness, for example, over a wide range while still meeting these criteria, thus relieving the user from the burden of optical source adjustment. Thresholding and rescaling the image data from a single image frame can thus yield both a represented reflectance image and a partially-thresholded fluorescence image, which permits both reflectance and fluorescence imagery to be acquired at the full frame rate of the optical sensor, in contradistinction with imaging systems of related art.

Example of an Embodiment of the Imaging System.

Figure 1B:
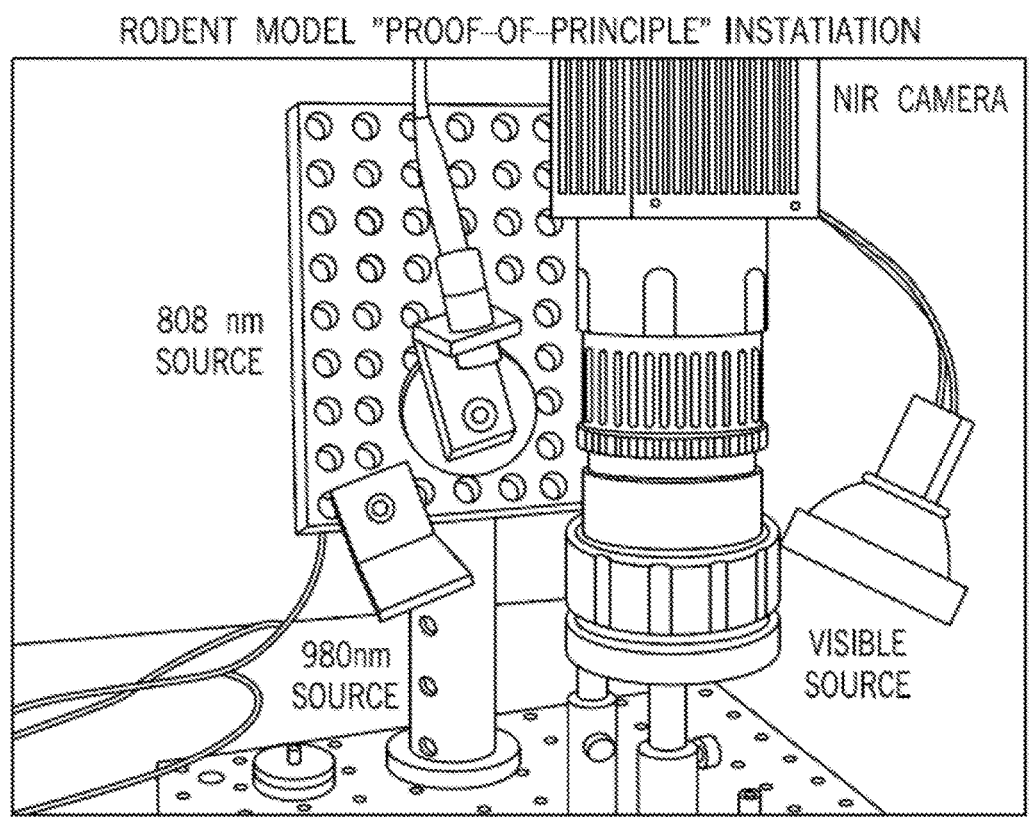
FIG. 1B provides a snap-shot image of the practical implementation of the embodiment of FIG. 1A.

An embodiment 100 of the imaging system of the invention is illustrated schematically in FIG. 1A. FIG. 1B provides an image of a working model of the embodiment 100. A chosen target or object 114 is positioned on a supporting frame 118 to be irradiated with light delivered (as shown with arrows 120A, 124A, 128A) from any of the light sources 120, 124, and 128. In one example, the light source 120, configured to transmit visible light 120A towards the object 114A, includes a standard 12 Volt MR-16 size "white" LED light source and Schott KG-3 visible-light-pass absorption filter (not shown). The source 124 of NIR light includes an unfiltered LED source (Marubeni: L970-66-60), interchangeably referred to as an "in-band source", configured to generate light at a wavelength within the NIR-II pass-band of the optical detection system discussed below (for example, at 980 nm). The source 128 contains an 808 nm fiber-coupled IR laser diode (Roithner: RLCO-808-1000-F), the light output of which is fed through an SMA collimator (Thorlabs: F240SMA-780; to control the size of the illuminated region) and a bandpass filter (CVI: F70-800.0-4-25.0M) to block low-level broadband optical emission from the light source. Optical sources 120, 124, 128 and/or the frame 118 are disposed on a baseplate (such as that by Thorlabs or Newport; not shown) and are appropriately equipped with standard optomechanical positioning hardware (such as positioning stages and rails, known in the art) that, in one case, is programmably-governed by a computer processor.

While the operation of the system of the invention is discussed below using a specific example of a tumor associated with a biological tissue, it is appreciated that such example is one example only and, in general, the system is intended to be used for acquisition and processing of optical data representing fluorescence of markers (such as fluorophores) associated with various targets embedded in or otherwise associated with a given object (whether close to the surface of the object or at a certain identified depth therein). Accordingly, neither the disclosure nor the claims appended to this disclosure should be, or are intended to be, interpreted as or limited by being directed to a biological tissue and/or the manipulations of or directed at such tissue.

Light 130 from the irradiated object 114 (which includes any light caused by irradiation of the object with any of the sources 120, 124, 128) is captured by an optical detection system 134 that contains the only single-optical-detector camera 138 operating in the NIR-II band of wavelengths (and, if required, is appropriately equipped with an optical lens collecting the incoming light) and a judiciously chosen optical long-pass filter 142 (which, in some implementations is optional). In one example, the system 134 contains a high dynamic range (14 bit) NIR imager and stock lens (such as Goodrich: SU320KTX-1.7RT), a 1.5" extender ring, and a Semrock 830 nm long-pass filter (BLP01-830R-50).

At least the optical detection system 134 is operably connected with a data-processing system 146, which includes a programmable processor (not shown) cooperated with a suitable frame grabber, and tangible, non-transient storage medium (not shown) containing software algorithms for image processing, recording, and display of optical data acquired with the use of the system 100. The storage medium additionally contains a hardware-control algorithm(s) that is configured to effectuate temporal multiplexing of operation of any of the three illumination sources 120, 124, 128 for a single source image or fused images for display and/or subsequent image processing. Additional optional components of the system 100 features (not shown) may include a display or monitor equipped with LED backlighting, or any other non-NIR-II emitting display, to reduce NIR-II band emission, user or processor-adjustable laser pump, in-band, and visible light power levels, and independent footswitch controls for all light sources to enable the user to manually select and operate each source while maintaining a sterile field.

It is appreciated that the use of light source or sources in the NIR-II spectral band defined by the sensitivity of the camera 138 facilitates the imaging of a portion of the object (tissue) at greater depth. But when used in combination with a fluorophore that emits in the NIR-II band, the amount of autofluorescence created by endogenous fluorophores present within normal tissue is reduced. Additionally, tumor detection in the NIR-II spectral band allows the additional and/or complementary use of visible illumination of the same object during the entire surgical procedure without detrimental effects on the results of the NIR-II based imaging. For example, the use of LED-containing light sources used for surgical illumination (such as the Steris Harmony LED 585 for example, with minor modifications such as the addition of KG-3 filtering) does not produce any practically-significant impact on the process of fluorescence detection.

Figure 2:
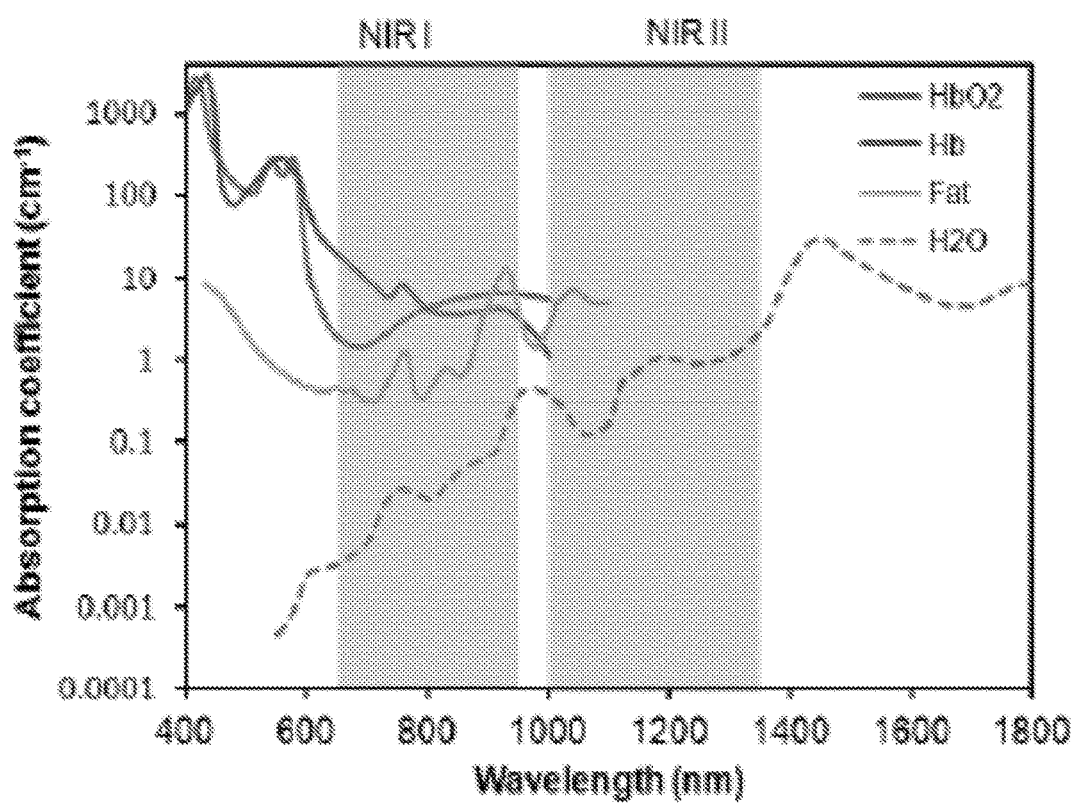
FIG. 2 contains plots representing optical absorption characteristics of identified biological components.

FIG. 2 presents curves illustrating typical absorption characteristics of identified components of the biological tissue across the visible, NIR-I and NIR-II spectral regions.

According to one implementation, the imaging of the object utilizes fluorophore(s) that have affinity to tumors and that are judiciously defined to be excitable at multiple discrete pump wavelengths, or, alternatively, within a broad spectral region (by both visible and NIR pump light sources) across which the extinction depth varies in the turbid media being examined, in combination with tunable or fixed pump sources emitting within this region (visible and NIR-I band pump sources). Examples of such functional fluorophores are provided in US Patent Application Publication no. 2013/0230464, which is incorporated herein by reference in its entirety.

Fluorophores.

The NIR-II fluorophores of choice are conjugated to tumor-selective probes as agents for contrast-enhanced optical imaging of the tissue according to an embodiment of the invention. Specifically, genetically engineered M13 bacteriophage is used as a biological scaffold, playing the role of a multifunctional carrier vector for achieving (1i) a well dispersed aqueous suspension of NIR-II probes, for example single-walled carbon nanotubes (SWNTs), without additional chemical functionalization, which retains sufficiently high photoluminescence of the NIR-II emitters for high-quality fluorescence imaging, (ii) a highly specific tumor targeting agent through a receptor-binding peptide conjugated onto the terminal capsid protein (p3) of the M13 virus. For example, in one implementation, SPARC (Secreted Protein, Acidic, and Rich in Cysteine)-binding peptide engineered on the p3 (SBP-M13-SWNT) was used for active targeting against the OVCAR8-IP human ovarian cancer cell line (used in our animal models) overexpressing the matricellular protein SPARC. More generically, the p3 can be suitably modified to attach other moieties such as anti-folate receptor, for targeting Folate Receptor-alpha overexpressed in 0.90% of epithelial ovarian cancers, for example.

It is appreciated that biocompatible NIR-II fluorophores (such as SWNTs or quantum dots) or downconversion nanoparticles such as lanthanide-doped NaYF4 fluorides) are attractive candidates for use as fluorophores in NIR-II imaging in an appropriate situation, because such fluorophores photoluminesce in the 1.1-1.4 μm range, exhibit large Stokes' shift between excitation and emission, and are distinguishable from the low autofluorescence emitted by normal tissue in this spectral band of optical waves. In addition, these fluorophores are highly resistant to photobleaching (as compared to organic dyes, for instance), can be functionalized with targeting/drug delivery agents, and exhibit high optical absorbance in NIR-I offering the additional possibility of photothermal therapy. To the best of the knowledge of the Applicants, related art is silent with respect to, and has not yet achieved, actively targeted fluorescence imaging in vivo of sub-mm size tumors during an image-guided procedure(s) conducted in the NIR-II spectral band. Similarly, while rare-earth doped fluorides have been shown to accumulate in tumor tissue following localized intratumoral bolus injection, there has been no reported work demonstrating actively targeted real time imaging and detection, of tumors in live subjects using these materials, through a more generally applicable systemic injection. For the purposes of this disclosure and accompanying claims, a real-time performance of a system is understood as performance which is subject to operational deadlines from a given event to a system's response to that event. Embodiments of the invention employ NIR-II fluorescent probes for in-vivo targeted imaging for cancer detection purposes, or during real-time surgical tumor resection, neither of which has been demonstrated by related art.

The use of NIR-II fluorophores (such as SWNTs or downconversion nanoparticles) in an embodiment of the present invention facilitates the use of high-irradiance continuous-wave laser excitation of the tissue, in one embodiment, at a level of tissue irradiance of about 30 mW per cm$^2$, which is still an order of magnitude lower than the maximum permissible values for acceptable irradiance on skin estimated according to the International Commission on Non-Ionizing Radiation Protection 2013 guidelines to be ~3800 mW per cm$^2$ for 1 s continuous wave exposure for 400 nm<λ<1400 nm). By comparison, small-molecule fluorophores such as Indocyanine green suffer from "photobleaching" irradiance of light in excess of 50 mW per cm$^2$ is known to cause irreversible chemical changes, with subsequent loss of fluorescent behavior.

The use of such fluorophores (and, in particular, the use of SWNT) in juxtaposition with the object (tissue, in one non-limiting example) in an embodiment of the present invention facilitates the inference of the depth and morphology of multiple fluorescent loci (SWNT-tagged tumors) within the turbid media (both during surgery and transcutaneously prior to surgery) from the optically acquired imaging data. Typical practical (for the purposes of this disclosure) depths of penetration of shorter wavelengths of visible light into the biological tissue do not exceed a few mm, which limits the excitation of fluorescence caused by such light to fluorescence only in shallow-located tumors. The practical depth of penetration of the NIR-I pump light, on the other hand, is on the order of several centimeters (for example, 3 cm), leading to the excitation of both shallow and deeper-located tumors. Thus, scaling and differencing the resulting NIR-II imagery can be used to infer tumor depth and tumor morphology. It also enables the rejection of confounds from various artifacts present at the object tissue, such as, for example, tattoos, scars, and injection site artifacts.

Accordingly, a skilled artisan will readily appreciate that the proposed triple-illumination intra-operative optical configuration provides operational advantages over the imaging systems of related art. Indeed:

Optical NIR-II fluorescence imaging offers significant advantages over current established imaging techniques, because: (a) unlike CT, which exposes the patient to large doses of ionizing X-ray radiation—optical imaging relies instead on non-ionizing optical wavelengths; and (b) unlike MRI, which is an expensive technique, is incompatible with magnetic materials both in and near the patient, and requires specialized operator training—optical imaging can be implemented at a fraction of the cost, with minimal operator training, and is unaffected by proximity to conductive metallic materials (pacemakers, infusion pumps) or small magnetic objects (steel shrapnel) within the patient. Moreover, unlike systems for CT or MRI, which both require the use of large and heavy equipment, Optical NIR-II fluorescence imagers can be designed as lightweight (<10 kg in one non-limiting example) portable instruments capable of operating on battery power (together with a laptop computer and associated algorithms), and easily carried by a single individual.

The use of the LED-based source of visible light simultaneously enables the illumination of the object in the visible portion of the spectrum with a high color rendering index (unlike some NIR-I band instruments) and provides a real-time fluorescence imaging capability. (In one embodiment, the visible source 120 is a continuous source that can be modulated and/or temporally multiplexed with other light sources).

The use of a single additional "in-band" light source 124 judiciously configured to emit light 124A at a wavelength within the passband of the (NIR-II) imager 134 in a fluorescence imaging system, to produce (in reflection from the object 114, forming a portion of light 130) a monochrome image that, as seen by the camera 138, contains the same or similar optical features as those in the image formed by visible light and perceived by an eye, revealing the morphology and surface detail of the object 114 in the in-band light. The wavelength of this "in-band" light 124A can be chosen, in one implementation of the invention, to coincide with an absorption band of the tissue (the 960 nm or 1400 nm water absorption bands, for example) to intentionally reduce the absorption depth in tissue to more closely approximate the shallow optical extinction behavior of visible light. Moreover, in comparison with the visible light 120A, the wavelength of the in-band light 124A can instead be chosen to penetrate deeper into the object 11, revealing features below the object surface and perceived in reflectance of light. Also, with time-division multiplexing between two or more in-band source wavelengths, a pseudo-color image can be created which is more visually informative than the monochrome image provided by a single in-band source wavelength. Such use of an "in-band" light source 124 (to create an intuitive reflectance image of the object that mimics the objects appearance in the visible portion of the optical spectrum as perceived by an eye and/or to reveal subsurface targets), in combination with the high-quality spatial registration afforded by the use of a single optical camera 138, greatly enhances the fidelity and registration of the processed data product (superimposed tumor visualization) with minimal computational burden. With the use of an embodiment of this system, for example, the user is enabled to view a real-time display showing highlighted tumor locations superimposed on a visually intuitive "visible-like" reflectance-mode image of the surgical field, even as resection of those tumors is being performed.

The use of an "in-band" light source 124 judiciously configured to emit light at a wavelength within the passband of the (NIR-II) imager in a fluorescence imaging system that reveals the morphology and surface detail of the object in the in-band light enables the use of "non-rigid body" image processing algorithms. These algorithms, if provided with data representing sharp image detail (such as data acquired in light of the light source 124 that has been reflected off the object), are structured to correct the imaging errors caused by target motion within the field-of-view, thereby enabling significant improvement in the fluorescence image contrast and signal-to-noise ratio of the imagery when small object motion is present. (Non-limiting examples of such motion include respiratory and cardiac motion of tissue.)

The addition of the laser pump source 128 facilitates the excitation of fluorescence in the object, while the use of a single InGaAs imager system to acquire light 130 (including a portion of light 120A, a portion of light 124A, and fluorescence excited with light 128A) enables inherent, automatic (passive), and permanent collocation of images formed at the wavelengths of light 130. (As long as the image is in focus, reflectance and fluorescence images will always be collocated and perfectly registered within the chromatic limits of the lens).

It would also be appreciated by a person of ordinary skill in the art that pumping the object with irradiating light in the visible and/or NIR-I bands (light 120A, 128A) and detection in the NIR-II band (light 130) additionally simplifies spectral filtering requirements, because it provides a wide spectral transition band over which spectral blocking may be applied. This allows the use of less expensive optical filters with wider acceptance angles (which greatly improves light collection efficiency since "faster" lenses can be used), or the use of higher-performance filters to provide a wider dynamic range.

The use of a single optical camera 138 in the embodiment 100 of the invention offers high-quality spatial registration of images acquired at different wavelengths. This translates to a simpler, lighter, more rugged system design and simplified operation for the user (in that mechanical co-alignment or co-registration adjustment is never required, in contradistinction with dual-camera systems conventionally utilized in the related art).

Because the camera 138 is configured to detect fluorescence at wavelengths exceeding 1 micron, the color-rendering index (CRI) provided by the visible LED illumination source 120 can be higher than that of fluorescence imaging systems of related art that operate within the first biological window (NIR-I, ~600 nm to 900 nm), thus providing better image-rendering of the object 114 for the user. For example, the user then has a flexibility of performing manipulation of the object with the visible light with the use of the LED source 120 to illuminate the field and be guided "by eye", while simultaneously observing the object in a fluorescence mode of operation of an embodiment (during which the user can alternate between an inherently perfectly-registered reflectance image, obtained at the wavelengths of light 124A for anatomical context, and fluorescence image for detection of tumors). The two images as well as automatically-segmented tumor detection masks can be overlaid on the monitor.

Depending on the particular mode of operation, the light sources 120, 124, 128 can be operated sequentially, be temporally multiplexed, or be operated simultaneously. Since power outputs from the light sources are independently adjustable, the fluorescence and reflectance imagery can be separated in the amplitude-domain (for example, by thresholding the imagery such that the fluorescence display shows only detected intensities above 1600 counts while the reflectance display shows imagery between zero and 1600 counts). This method facilitates the formation of high-quality fluorescence and reflectance images, while also enabling full visible illumination of object with all three light sources 120, 124, and 128 operating simultaneously. Based on information available to-date in the related art, the simultaneous operation of all three light sources has not been considered in the case of combining the irradiation of the object with light from the in-band light source with light from the NIR-I pump light source, as well as in the case of combined irradiation with light from the in-band light source with irradiation with the visible light to generate real-time self-registered fused images with the use of a single camera for an image guided application.

It is also appreciated that embodiments of the invention are compatible with the use of multiple NIR-II emitting fluorophores (such as SWNT, quantum dots, or upconverting luminescent materials), utilized either alone or in combination and judiciously functionalized to have affinity to identified targets (in one example—targeted tumors).

Methodology.

An embodiment of the system of the invention (such as the embodiment 100 of FIG. 1) is complemented with algorithms implemented in computer-program codes that include at least:

Hardware control software for operation of the optical detection system 134 and illumination sources 120, 124, 128 (either independently or in concert, simultaneously or in sequence, based on a user selection in real-time or in a pre-programmed fashion A visualization interface to display raw or processed imagery with user-selectable processing and display options with products unique to triple illumination/single camera hardware configuration, and The program codes governing data processing and display/visualization interface, which are loaded on the storage medium of the unit 146.

Visualization Interface

Figure 3A:
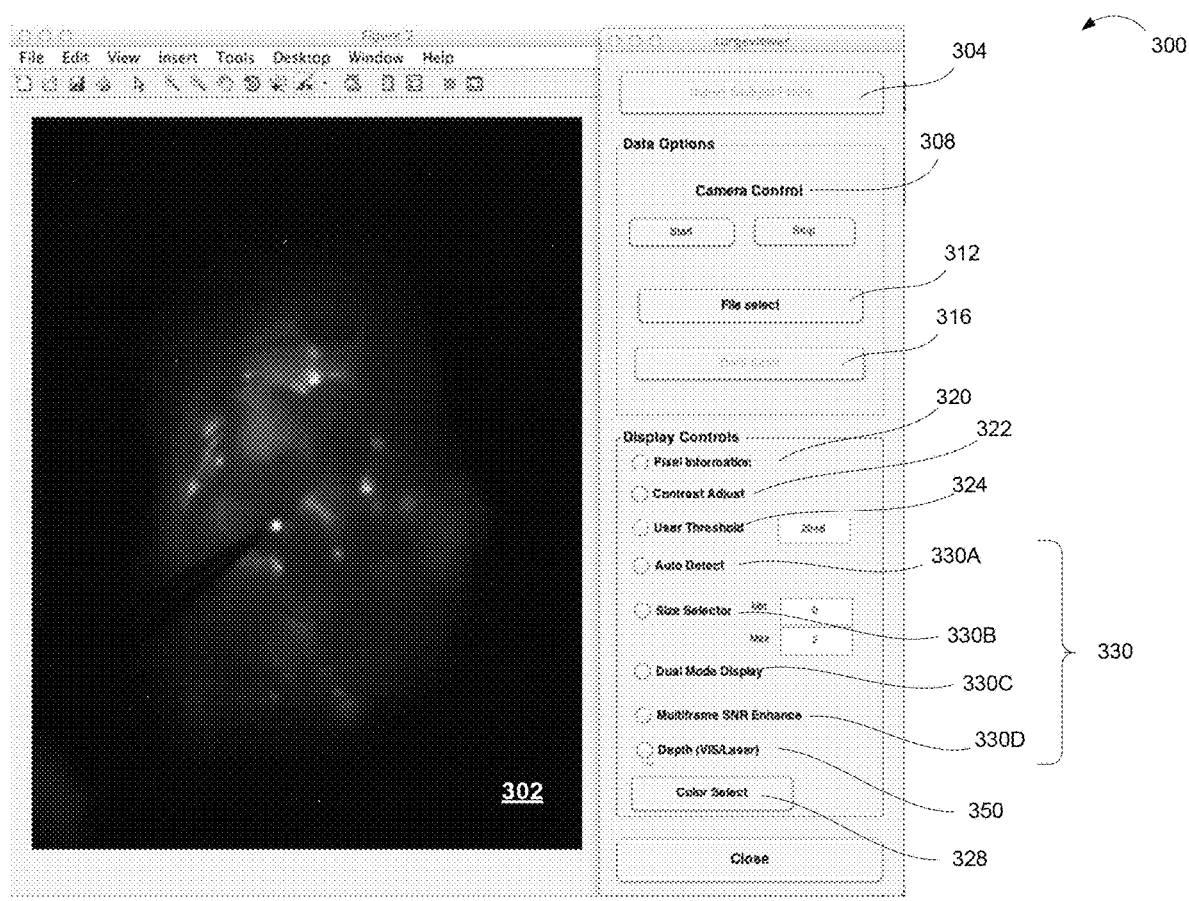

An example of a corresponding visualization display is shown in FIG. 3A in the form of an interactive data viewer interface 300 (to which any of multiple user-defined inputs may be entered, for example a user-defined input representing a size threshold for tumor detection).

The following describes, without limitation, various features of the user interface. Generally, the visual manifestation of the interface as presented to the user on a monitor such as a computer monitor, for example, includes a resizable display window 302, virtual buttons and/or activators and/or menus (labeled with visual indicia such as "Input Subject Info" button, "Camera Control" button, "Pixel Information" actuator, or "Dual Mode Display" actuator, to name just a few) that, when activated by the user, trigger or initiate at least one of the following functionalities of an embodiment of the invention.

The "Input Subject Info" or an equivalent activator 304, is configured to accept, load and use subject-identifying information, data formatted, for example, as a .txt type of data file. Governing of live, real-time stream of data received from the optical detector/camera is carried out with the use of controls 308 under the general rubric of "Camera Control". Data-file selection from user-selectable directories (tangible data storage) is triggered in response to user-activation of the "File select" button 312. The system is configured to save/store data into a custom-formatted data file (such as, for example, a file formatted as .bimg or .avi) in response to activation of the "Data Save" activator 316. Display controls 320, 322, 324 are configured to control level of irradiance (brightness) of display pixels in a user-defined window; the use of a histogram to select a set of display dynamic range, and a choice of a constant threshold for specific data acquisition (such as, in one example, tumor detection). The GUI 330 is additionally configured to present visual assessment at least one "overlay" representing results of the detection on top of the image in the display window 302, the color of which overlay is controlled with the actuator 328. The group of features 330 that advantageously distinguish an embodiment of the invention from known related art includes the initiator 330A of a detection modality utilizing a multi-scale detection; initiator 330B of a user-selectable target (tumor) size display configured for operation with a range of target sizes expressed, for example, in cm; an actuator 330C of a display mode that leverages multi-source (in-band and laser sources) to display perfectly registered reflectance and laser-fluorescence images acquired with an optical detection system of an embodiment; and a control 330D associated with formation of a depth-map representing location of a target in the object and showing the distribution of contrast of a signal, received from the target, in a two dimensional form (X-by-Y image) or in a three-dimensional form (X-by-Y image vs. depth) based on data received from multiple spectral bands, for example, within the visible spectral band, and/or spectral band associated with the laser source as in the embodiment of the invention.

An embodiment of the invention may be configured to load and use, at the user's input, standard text file(s) and/or ASCII files. Optionally, the interface may be adapted to operate with multiple text files (for example, files in multiple languages with a default of English language) associated with the chosen individual image frame or a video.

FIGS. 3B, 3C, 3D, 3E, and 3F provide examples of operation of the interface 300 in response to and during the interaction with the user in real time.

Figure 3B:
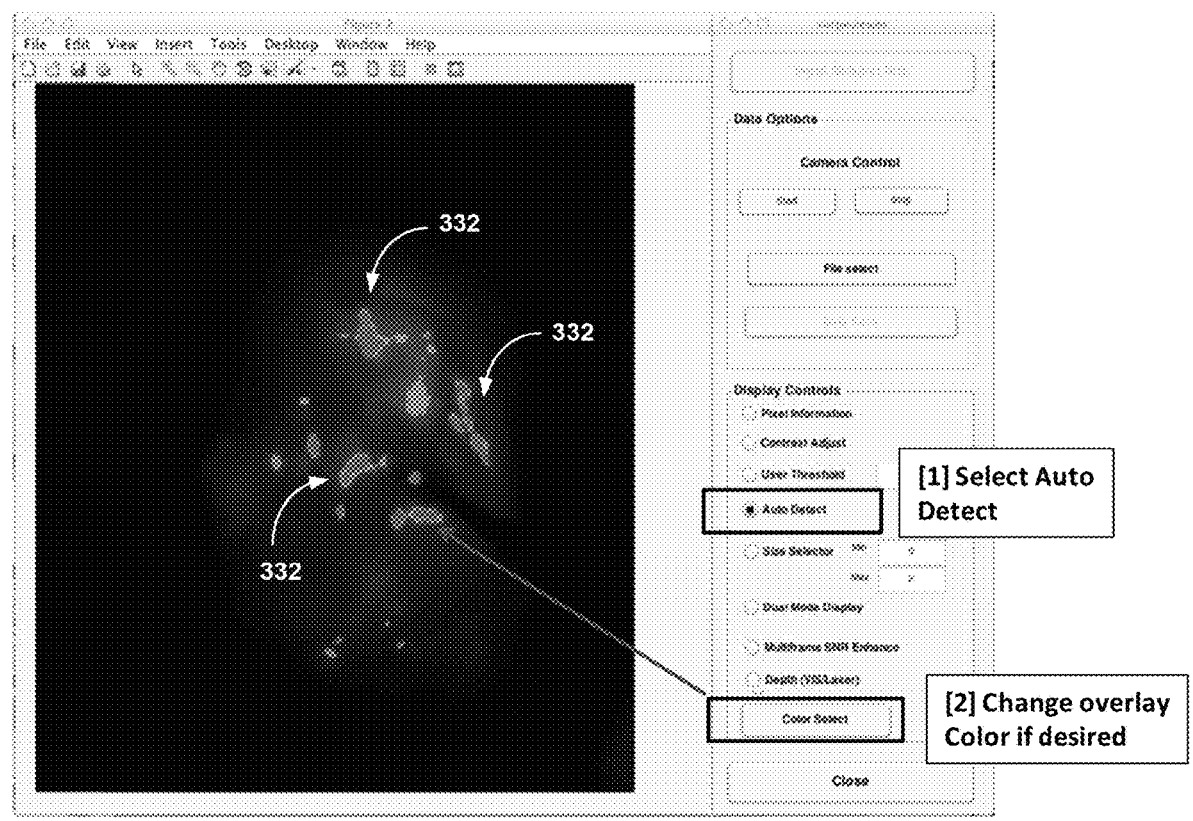

FIG. 3B shows a screen-shot of an image 302 of FIG. 3A on top of which an overlay 332, indicated with image areas 332 of chosen color, is added as a result of operation of the auto-detection modality 330A as defined by the user. This is achieved, in practice, by activating, 1, the "Auto Detect" feature of the embodiment of the invention followed by a change of the color of the overlay data, 2, if so desired.

Figure 3C:
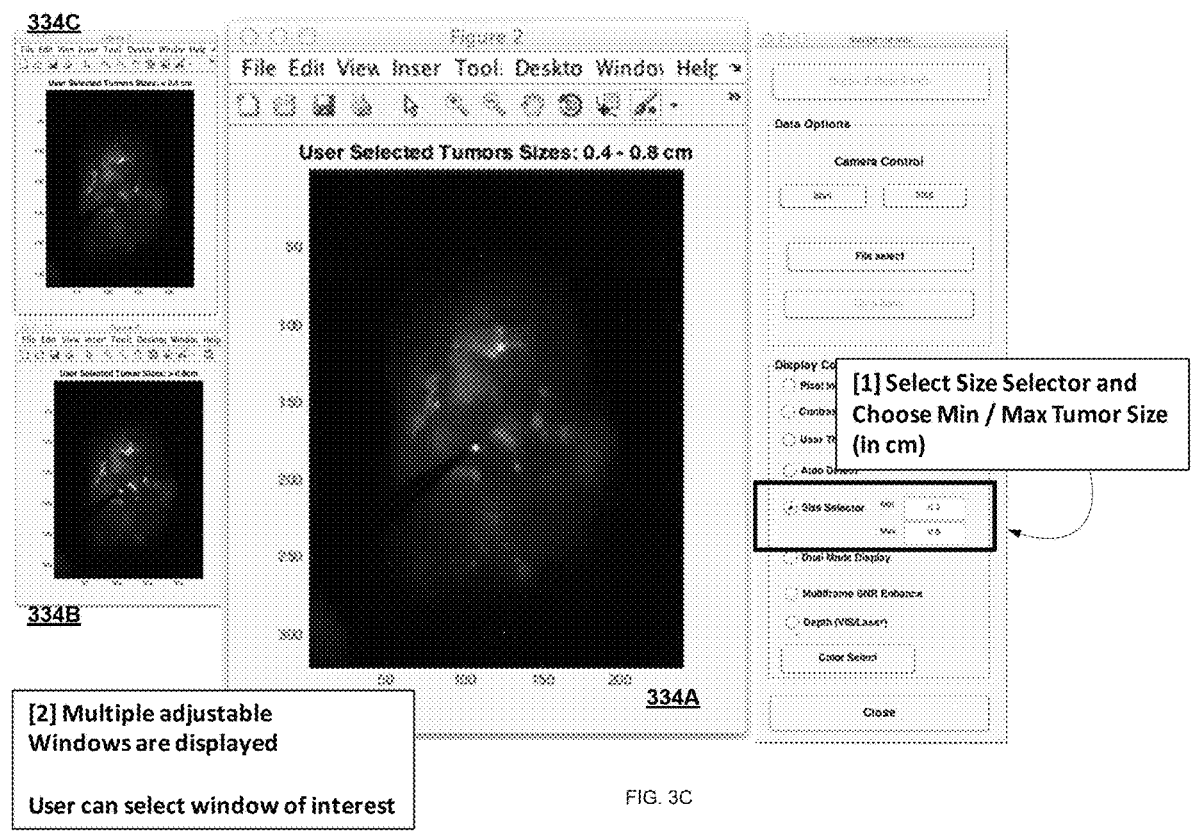

FIG. 3C illustrates multiple adjustable windows 334A, 334B, and 334C, produced as part of the operation of the interface 300 in response to user-inputs identified in FIG. 3C as steps 1 and 2, and providing visualization of results of imaging produced by analogy with that of FIG. 3B. The Images displayed in windows 334A, 334B, 334C of FIG.

3C, however, are additionally adjusted with respect to spatial dimensions and according to the activation of the target size selector 330B.

Figure 3D:

FIG. 3D presents elements of the interface and menu of an embodiment of the invention representing multi-frame signal-to-noise ratio and a dual-mode display screenshot, selected for visualization of either both of reflectance and fluorescence images or only a fluorescence image, as acquired with an embodiment of the invention. In the specific example shown, as a result of selecting multi-frame data processing (by activating, 338, an actuator 330D in window 336) and selecting images data files (by choosing, 340, a button 312 in window 336A and then specifying the type of data files, in window 336B for live stream of data or, if saved files selected, choosing them, 342, from the directory of window 336C), an output registered fused image 344 is displayed in window 336D. Such fused image provides for visualization the chosen image data and can be further enhanced with selection of a histogram 346 (in window 336E) in response to user-input 348 activating, in window 336A, a dual-mode display to visualize either both the reflectance and fluorescence imagery or just fluorescence imagery acquired with an embodiment of the system of the invention.

Figure 3E:
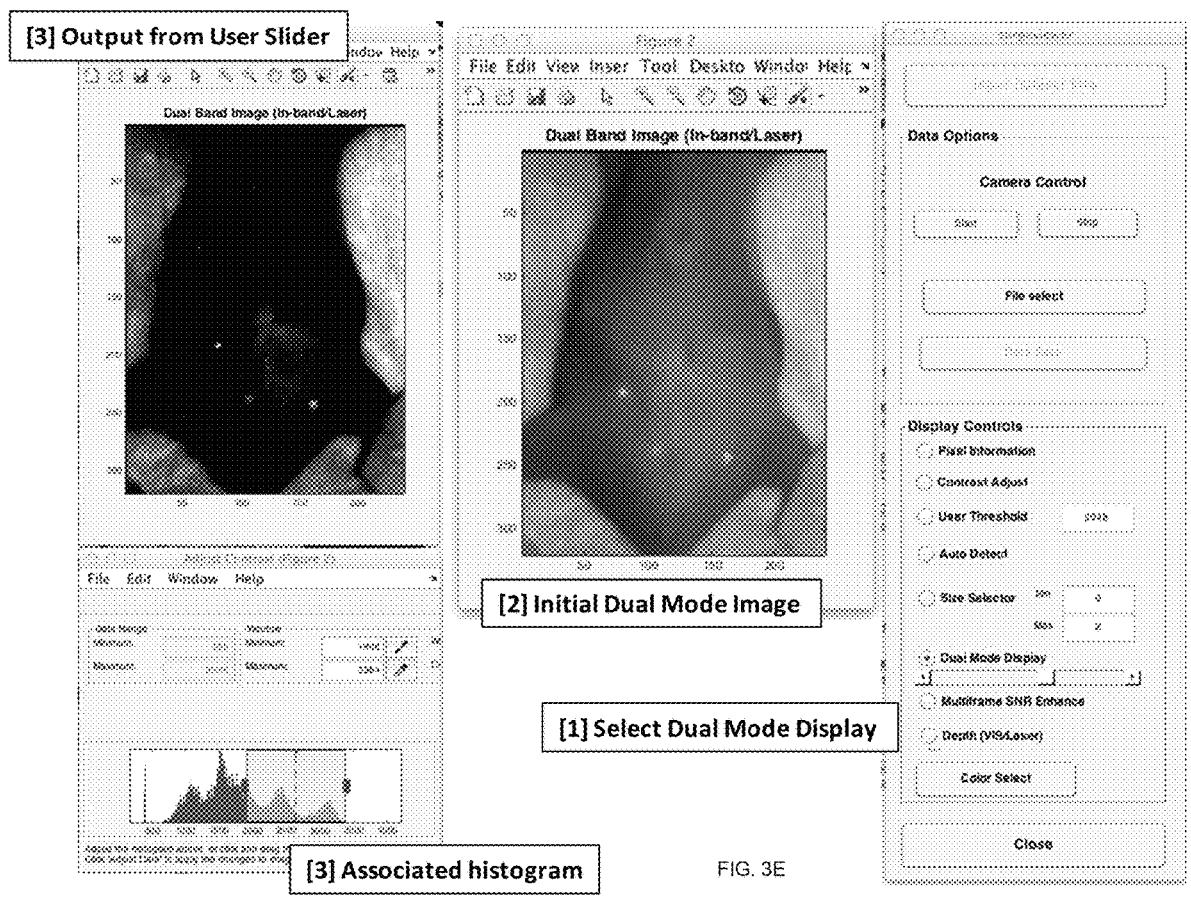

FIG. 3E illustrates a related screenshot of an interface of the embodiment configured to operate in a dual display mode, 1, and presenting for visualization an initial dual mode image 2 together with an output from user slider and the associated interactive histogram, 3, configured to accept the user-defined input representing a minimum value of threshold for tumor detection.

FIG. 3F illustrates an additional feature of an embodiment representing operation of the interface 300 to present and analyze depth map information related to the target. Here, in response to a user-input to activate 1 of a "Depth" activator 350 of the interface 300 (see FIG. 3A) as well as the selection of a data set representing either visible image of the target or/and an image acquired in light of the laser source, 2, the computer-processor of the embodiment of the invention displays an additional GUI window (that is user-adjustable with respect to the several operational image parameters such as, for example, zoon, aspect and/or rotation angles) to form an surface contour 354 representing an estimated depth map of the imaged target.

Methodologies for Governing Data Processing and Display/ Visualization Interface Include:

A) Real-time automated detection of targets at the object based on user-selected target-size threshold. The corresponding algorithm is configured to generate a binary or graded detection map of tumors and code for near-real-time multi-scale constant false alarm rate (CFAR) target detection (in one specific case—tumor detection) algorithm. The multi-scale CFAR detector algorithm includes multiple multi-scale data processing kernels (such as mean or median filters, Gaussian filters, and wavelet bank, for example). In operation, each of the kernels may be convolved with the image distribution. A detection threshold is chosen to meet constant false alarm rate criterion generating a binary image at multiple scales. These binary images can be combined using a decision logic to create a single binary image, one example method being application of a per pixel based "and" operation across all binary images generated at multiple scales; another example method being a refinement based criteria where smaller scale binary detection map pixels supersedes larger scale detection map pixels when overlapped. The output is a binary image representing a detection map with tumors indicated in the image and segmented by size and/or morphology by use of any binary or graded image filtering processing that includes pixel clustering, segmentation and labeling, which may be further interactively filtered by the surgeon to choose minimal desired detectable tumor size.

Figures 4A, 4B, 4C:
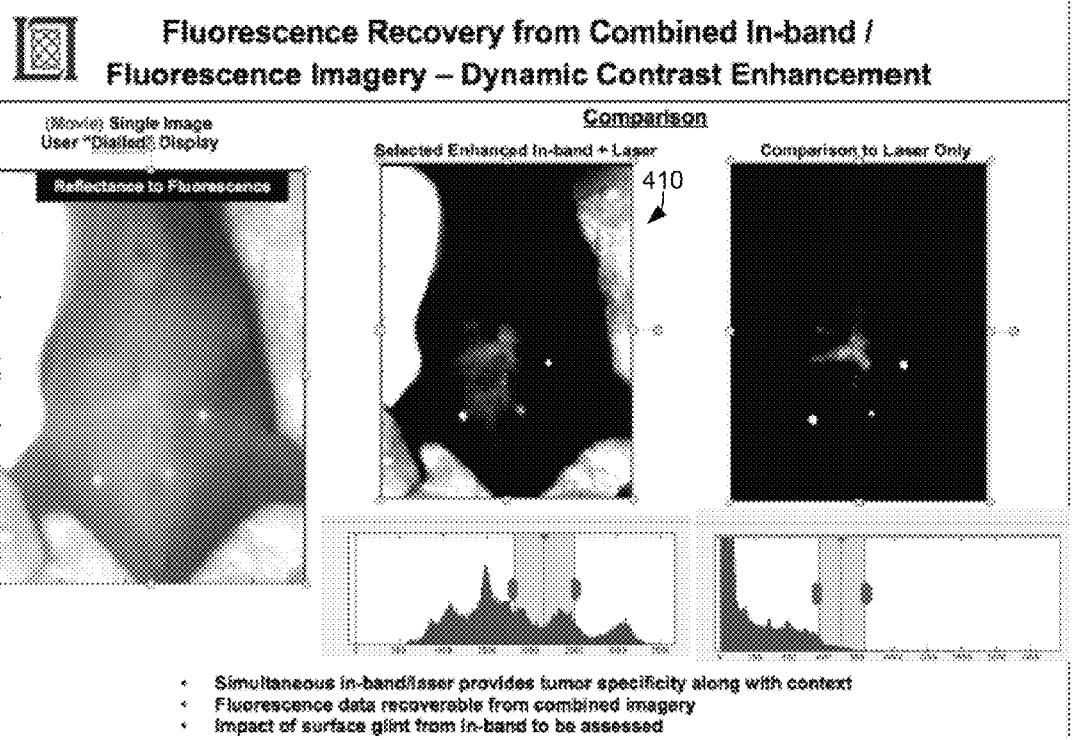
FIGS. 4A, 4B, 4C illustrate leveraging of irradiation of the object according to an embodiment of invention for generation of multiple unique registered single images or image sequences from single fused images or sequences of images.

B) Real-time automatic registration and fusion of imagery data and user-controlled dial-up display, configured to leverage simultaneous multi-source illumination of the object [for example, i) visible and in-band radiation provided by the sources 120 and 124, respectively; or ii) NIR pump source and in-band radiation, provided by the sources 124 and 128, respectively], functionalized fluorescent probes emitting in the NIR-II window, and a single-camera high dynamic range optical detection system 134 (FIGS. 4A, 4B, 4C). Following the simultaneous irradiation of the object with light from two light sources (dual-source illumination), the system automatically generates a single image frame of spatially co-registered and fused data containing both a contextual image acquired in reflection of light delivered from the in-band source 124, and a fluorescence image highlighting the location of the tumor in the object. Leveraging the large dynamic range of the camera and the wide pixel amplitude variability between the in-band and fluorescence signals, the user of the system produces an input to the system (a "dial up") that facilitates a real-time interactive pixel range display. For example, a "low dial" setting can be chosen to produce an overall image in which a portion produced by the reflectance (in-band) signal dominates or is more pronounced then the fluorescence-defined portion of the image. At the same time, "high dial settings" may be chosen to display an overall image in which the fluorescence-defines portion is more pronounced.

Figure 4D:
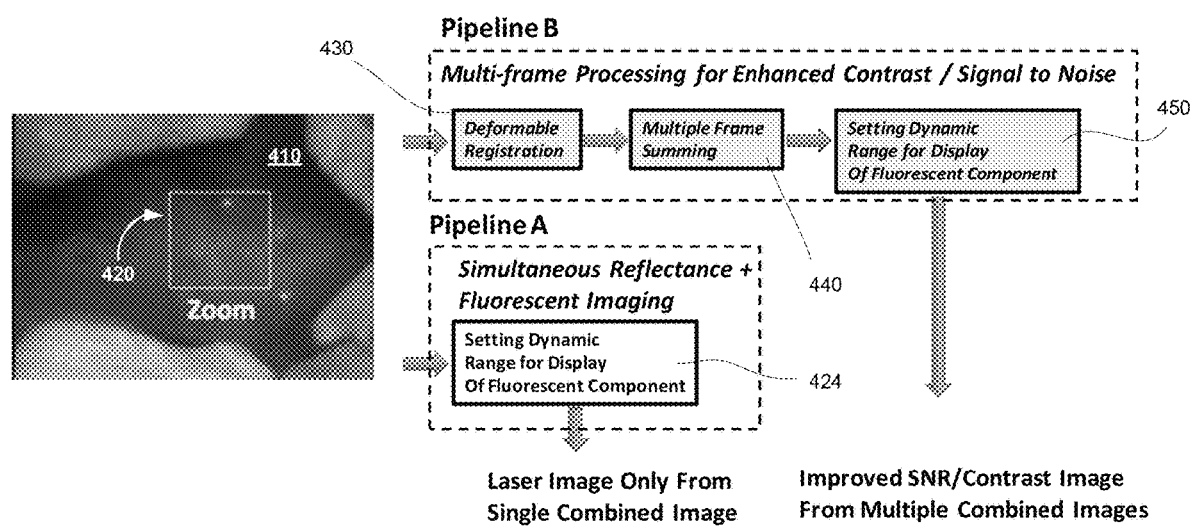
FIGS. 4D, 4E, 4F illustrate a process of leveraging irradiation of the object with deeply-penetrating light and the use of using multiple image frame data facilitating the generation of images that are characterized by enhanced contrast despite the presence of linear motion and/or elastic deformation of the object during image collection.

FIG. 4D provide additional illustration to the methodology of a multi-frame processing of a combined image output 410 of FIG. 4B, that resulted from the simultaneous use of the multi-illumination system as described above to produce enhancement of contrast and/or SNR of the final image. Here, as schematically shown by the portion of FIG. 4D labeled "pipeline A", at least a portion 420 of an image 410 of a target, acquired as a result of dual-band illumination is leveraged, 424, to display a combined reflectance and fluorescent image and/or can be adaptively rescaled to select only the fluorescent image. As a result of the application of the "pipeline B" methodology, that includes the use of a multiple image frames (from about >=2 frames up to several hundred frames) of the dual-illumination image 410 (laser+ in-band source), imaging contrast and SNR of the detection of a target under dim illumination conditions are increased.

According to the latter methodology, high contrast information from the embedded in-band reflectance component is leveraged, at step 430, for accurate deformable (or non-rigid) registration. A person of skill in the art will readily appreciate the need in such leveraging from the following:

Some of the objects being imaged (biological tissue being but one specific example) are not rigid but operably flexible. Such objects does not move as one rigid structure, with every point displaced the same amount. Instead, as such objects "flexes", it undergoes what is referred to as "nonrigid body" motion (where each point on the surface has its own motion model that is strongly correlated to neighboring points on the object, and becomes progressively independent of the motion of points further away). In an alignment process referred to as a nonrigid body registration, images of materials that undergo nonrigid body motion are aligned by processing the image data using specialized techniques one example of which is a so-called Demons registration algorithm. Once images have been aligned through the process of the nonrigid body registration, the quality of the resulting images can be further enhanced through the standard multi-frame processing, such as frame addition, to improve the signal-to-noise ratio.

Most nonrigid body registration algorithms require, for proper operation, images with sharp spatial features (high contrast edges, for example), because distinct spatial features act as reference points throughout the registration process. NIRF imaging, however, especially subsurface NIRF imaging, produces diffuse images with poor spatial contrast, which is caused by diffusion of light scattered within the object. So the sharp edges of targets embedded within a given object are hard to resolve due to the softening effect created by the diffuse scattering of the fluorescent light within the object. This loss of image sharpness limits the quality of the nonrigid body registration with diffusely-scattering materials (such as biological tissue, for example). In addition, NIRF images may contain few spatial features suitable for registration.

According to the idea and implementation(s) of the invention, the process of nonrigid body registration of the NIRF images is improved with the additional use of in-band reflectance images. Features of an object that are imaged in reflectance at the wavelengths of light from the in-band light source are located in the same region of the object from which the NIRF images are collected. Here, light produced by an in-band light source is used to generate a surface reflectance image of the object with a rich set of image features (since the majority of detected light travels ballistically both to and from the surface of the object). The nonrigid body registration process is then applied to provide good image stabilization. If the irradiation of the object with light from the "in-band" light source and light from the fluorescence pump light source are alternated in time (time-multiplexed) such that each consecutive pair of acquired image frames contains a reflectance image followed by a fluorescent image, any point on the reflectance image is correlated in time to the respectively-corresponding point on the fluorescent image. The features from the reflectance image can then be used to guide the non-rigid registration of both the reflectance image sequence and the fluorescence image sequence. As would be readily understood by a skilled artisan, such methodology greatly improves the registration accuracy of the fluorescence image sequence.

Figure 4E:
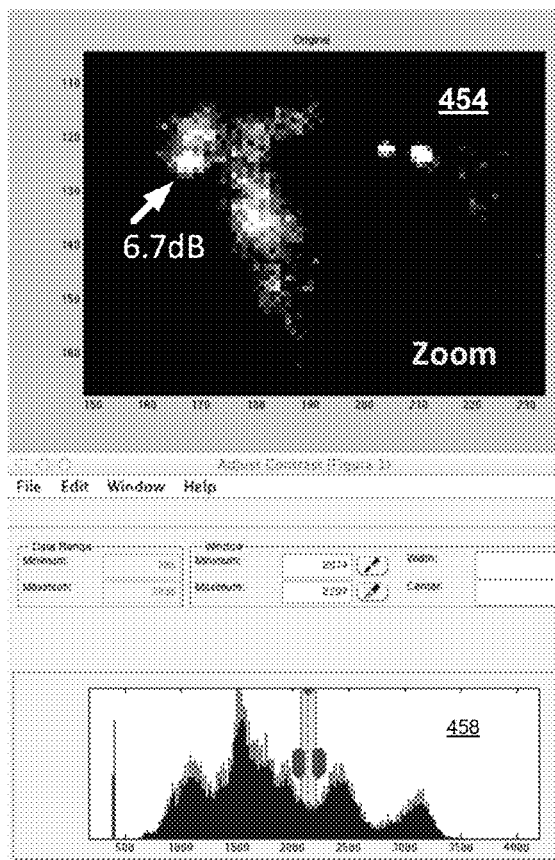
Figure 4F:
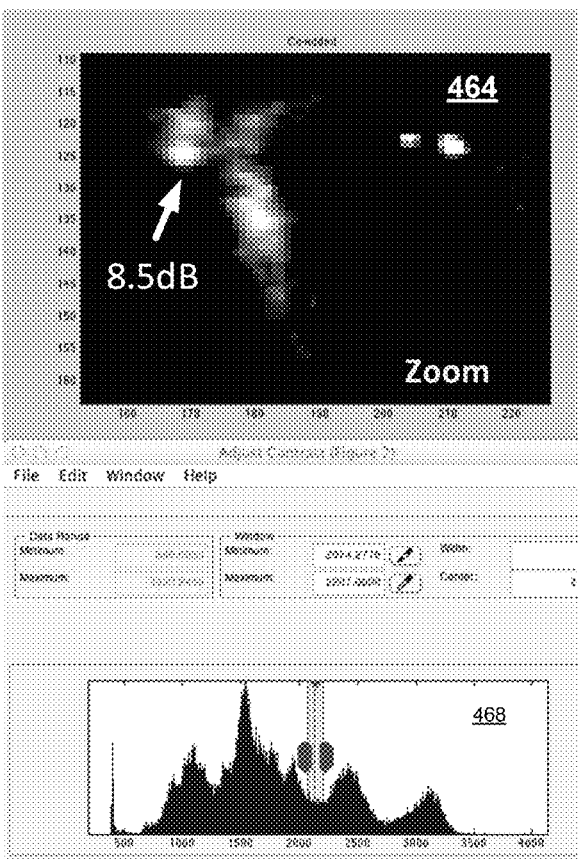

Referring again to FIG. 4D, multiple registered dual-band image frames are then summed, 440, to increase contrast and SNR. The resultant image is further redisplayed, at step 450, by setting dynamic range to show only laser induced fluorescence imagery with higher SNR/increased contrast as compared to a single image frame acquired conventionally with a single source NIR-II imaging modality of related art. To this end, FIG. 4E illustrates a single image resulting from the application of methodology "pipeline A" to a portion 420 of the combined image 410. The portion 420 is transformed to the image 454 by selection of the dynamic range of the image chosen according to the settings at the interactive histogram 458 to show the pixels of an image dominated by signal return from the illumination of the target with the laser-light. This is similar to adjusting the "brightness" and "contrast" controls on a display to accentuate only the targets of interest. FIG. 4F further illustrates an image resulting from the application of methodology "pipeline B" to a portion 420, which is transformed to an image 464 with SNR and image contrast that are enhanced, in comparison with those of the image 420, as a result of the application of multi-frame (>=2 frames) processing. Image 464 is redisplayed at the same dynamic range to compare the improved signal contrast.

Sequential portions of a computer-program code (Matlab®) effectuating the above-discussed multi-frame processing of image data, received with the use of an embodiment of the system employing dual-mode illumination as discussed, is illustrated in FIGS. 4G, 4H, 4i, and 4J.

C) Real-time automatic registration and display of the reference and fluorescent imagery through a "flicker" mode by leveraging sequentially carried out multi-source illumination (visible and in-band or NIR pump source and in-band, discussed below).

Figure 5A:
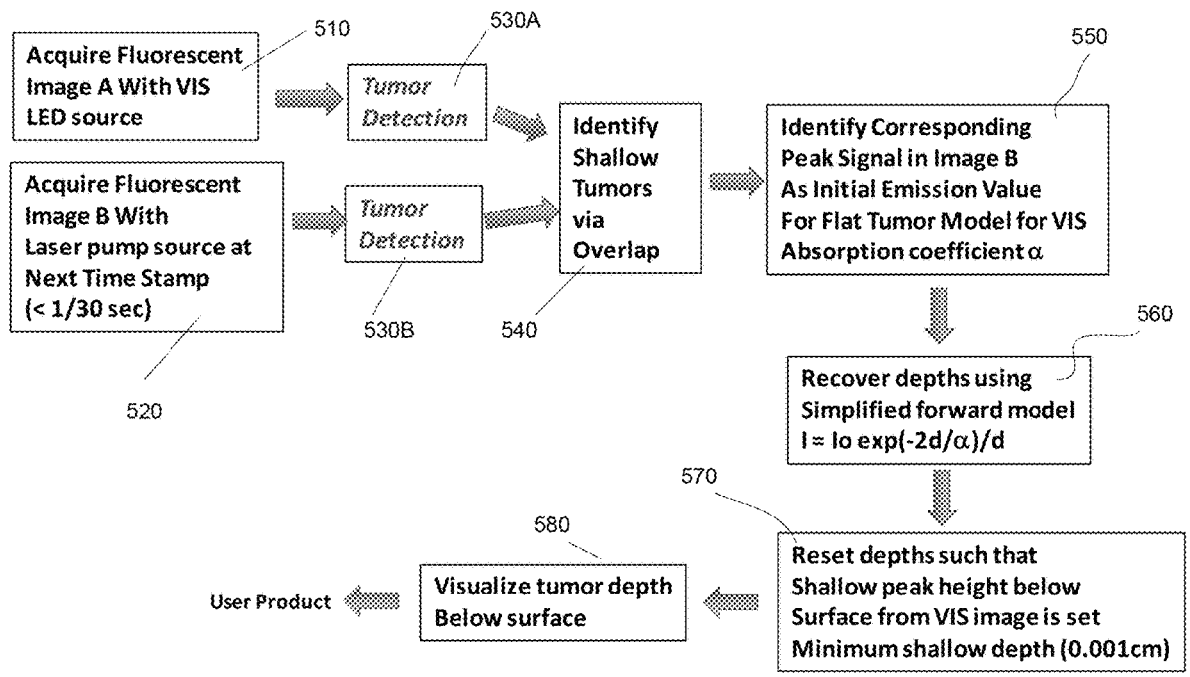
FIG. 5A is a flow-chart representing a process (and related program code) for recovery of a parameter of the depth, in the object, at which a target is located, based on an set of images sequentially acquired with the use of two types of light (light penetrating into the object only at a shallow depth and light penetrating into the object at a larger depth), as acquired with an embodiment of the invention.
Figure 5B:
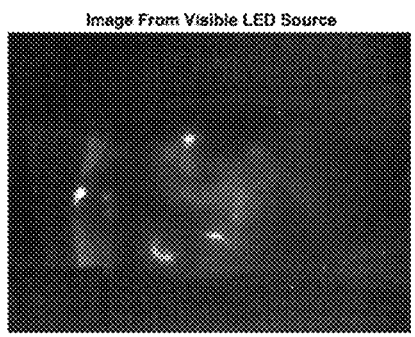
FIGS. 5B, 5C, 5D, and 5E show results of data processing to recover approximate depth of a target in the object and present, respectively, an image acquired with an embodiment of the invention, for estimation of depth of a target illuminated with: light from a visible LED source, which excites fluorescence while being attenuated within a few mm depth from the object's surface (FIG. 5B); light from a laser pump source, which excites fluorescence while penetrating tens of mm into the object (FIG. 5C); as well as images of targets and their estimated depths below the surface of the object, shown as a contour plot (FIG. 5D) and as a 3D-surface plot (FIG. 5E)
Figure 5C:
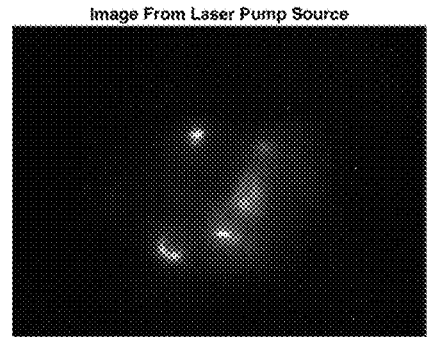
Figure 5D:
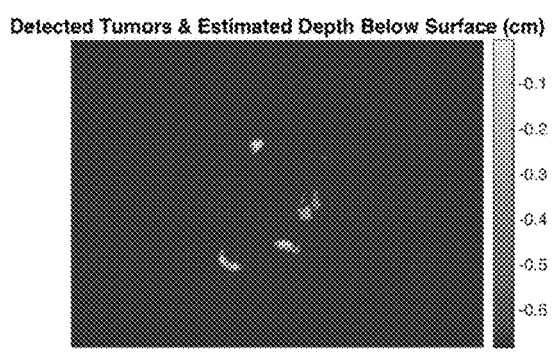
Figure 5E:
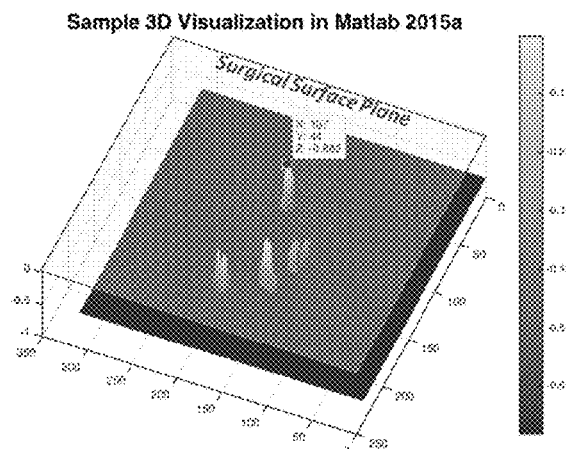

D) A flow-chart of method for recovery of a parameter representing location depth of a target imaged by a single camera possessing no parallax is illustrated in FIG. 5A.

A principle described below facilitates object-depth discrimination with the use of differential pump-light absorption in near-IR fluorescence (NIRF) imaging.

This methodology is based on or contingent upon choosing two (or more) fluorescence pump wavelengths that differ from one another sufficiently to ensure that the attenuation of light in the object (a combination of loss from both absorption and scattering) differs for these two wavelengths. An example of two such wavelengths of light for the object comprising a biological tissue includes the "A" wavelength chosen within the visible band between 400-700 nm, and the "B" wavelength chosen within the infrared band between 700 nm and 1000 nm, respectively.

In a specific case when the targets in the object are represented by tumors in biological tissue, and assuming that light at both "A" and "B" pump wavelengths has similar pump efficiency for pumping the fluorophore in both the shallow and deep tumors, if light at the pump wavelength "A" is strongly attenuated by the tissue, then the majority of its flux penetrates the tissue only a short distance. Therefore, the excitation of targets achieved with the use of light at the "A" wavelength is substantially limited to the excitation of surface or near-surface tumors. At the same time, if the pump light at the "B" wavelength is chosen to penetrate deeper in the tissue then the light at the "A" wavelength, then light at the "B" wavelength successfully excites both surface and deeper-lying tumors. While, overall, the deeper-located tumors receive less pump light due to both the attenuation of pump light at the "B" wavelength reaching them and to the attenuation of the emitted light that has to pass through a thicker layer of the tissue on its way back out to the detector, such misbalance can be compensated for algorithmically.

According to the idea of the invention, therefore, a NIRF image of the object is collected based on the excitation caused by the pump light at "A" wavelength only, while a second image of the object is formed based on the excitation caused by the pump light at the "B" wavelength only. By digitally "removing" the representation of object's targets present in both fluorescent images, only the representation of the deeper-located targets is maintained.

While the utilization of reflected (elastically scattered) light from the tissue by an "in-band" light source is not necessarily used in the implementation this method, the acquisition of such light can help in performing the unrelated process of tissue registration, described elsewhere in this application.

Accordingly, and referring again to FIG. 5A, two light sources are employed in a time-multiplexed fashion. The light outputs from these two light sources are chosen to penetrate into the object at different depths and cause, at such different depths, fluorescence of fluorophores associated with the object. At step 510, for example, light from a first light source is used to irradiate portions of the object (or targets in the object) located at a first depth and to produce fluorescent light at the fluorophores disposed at such targets. At the same time—in a time-multiplexing fashion (for example, with a <$\frac{1}{30}$ of a second switching period for a camera with a 30-frame-per-second video-recording rate)—or, alternatively, sequentially with light from a second light source is used to irradiate the object at step 520, to penetrate to a different second depth therein and cause fluorescence by the fluorophores disposed at targets located at the second depth. While not required, the operational wavelength of light generated by the first light source may be substantially equal to that of light generated by the second light source. In one example, the first depth is substantially a "skin depth" of the object, while the second depth is measured as ten(s) of millimeters.

Target detection at the first and second depths of the object is performed as a result of acquisition of fluorescent light emerging towards the optical detector from the first and second depths, respectively at steps 530A and 530B. The shallowly-disposed targets are effectively removed from the imagery by identification of those targets present in both 530A images and 530B images (at step 540), and setting the detection to surface-level tumors to estimate relative depth (step 580) of the deeper-located tumors based on the pump-caused scaled intensity of the fluorescence received from such tumors (steps 550, 560) under the assumption that the shallow tumors are located at a depth that is sufficiently small so as to be immediately visible to the user (570, for example, indicating some small value chosen to illustrate the skin-depth, for example 0.001 cm).

Practical advantages of the proposed approach are clear: the real-time differentiation between the weakly "glowing" fluorescent target located closer to the surface of the object from the target producing stronger fluorescence but located deeper in the object is effectuated without the use of a tomographic procedure conventionally used for such purpose in the related art. Moreover, such differentiation is carried out with an optical system that does not possess nor require optical parallax, by imaging the object and targets disposed at different depths within such object from the same angle (from a single spatial position) with parallax-free single optical camera from a single position. Alternatively, the camera can be used from multiple positions that are spatially shifted with respect to one another.

FIGS. 5B, 5C, 5D, and 5E present, respectively, an image acquired with an embodiment of the invention from a target illuminated with light from a visible LED source, at step 510;

an image acquired with an embodiment of the invention from a target illuminated with light from a laser pump source, at step 520;

targets, and their estimated depths below the surface of the object, shown as a contour plot and as a 3D-surface plot.

FIGS. 6A, 6B, 6C illustrate code for execution of the data-processing methodology and depth-differentiation of the multiple targets in the object disclosed in reference to FIG. 5A.

Overall, it is recognized and appreciated in the art that non-rigid registration of temporally-varying fluorescent imagery is challenging because of diminished contrast (manifesting, for example, in soft or blurred image edges and/or absence of reference features found for frame-to-frame NIR-I fluorescence imaging registration). As demonstrated above, the present invention includes an improvement of non-rigid registration of time-varying diffuse imaging, which turns at least in part on utilizing temporally interleaved illumination provided by in-band and Near-IR pump light sources, or interleaved illumination provided by in-band and simultaneous in-band and Near-IR pump light sources, and NIR-II emission of the functional fluorescent probes with the imager that is configured to collect optical data at frame rate defined such that the time difference between consecutive frames is much less than the time scale of motion of the object. An example is provided by an imager collecting first type of optical radiation at 60 fps with the interleaved optical radiation being collected at, for example, 30 fps. In this case, non-rigid registration techniques such as the standard Demons algorithm is applied, first to consecutive pairs of in-band images to defined-per-pixel motion for nonrigid body alignment. The resulting map of pixel motion map is scaled (for example, by a factor of two) and then applied to the intervening fluorescent image or the image representing the results of fusion of acquired in-band/fluorescent radiation for high-fidelity non-rigid registration. It is appreciated, therefore, that embodiments of the invention facilitate improvements of non-rigid registration to fluorescent imaging based on time-multiplexed illumination of the object, which is utilized for improved sensitivity in detecting smaller tumors or tumors that are at lower surface depths. In doing so, multiple frames N are added (via coherent integration, for example) to increase signal-to-noise ratio (SNR) by a factor of square root of N.

According to a related embodiment, discrimination between targets to be imaged (such as tumors) located at shallow depths ('surface targets') and deeper-located subsurface tumors is effectuated based on sequential (or time-multiplexed, "flicker"-type) excitation of fluorophores with visible and NIR-I pump source generated light in the imaging system of the invention. In one example, the irradiation of object with light at wavelength A (reaching shallow targets) can be followed by with irradiation of deeper-located targets with light as wavelength B, or vice versa. In another example, the irradiation of object with light at wavelength A (reaching only the shallow targets) can be followed by simultaneous irradiation of object with light at both wavelengths A and B (thus reaching both shallow and deeper-located targets).

The results and operational success of such implementation also stems from the difference in penetration depths for visible illumination and NIR light for the same fluorophore location. The results can generally be presented in a variety of ways, for example as a flicker image between visible and NIR-I pump source images, or as a relative depth map derived from image ratios using fixed tissue scattering/attenuation coefficients. A relative depth map can be derived from the image obtained at the wavelength of the NIR-I pump source (and containing identification of subsurface tumors) and that obtained with visible light (and containing visualization of surface tumors in the same object).

Figure 7A:
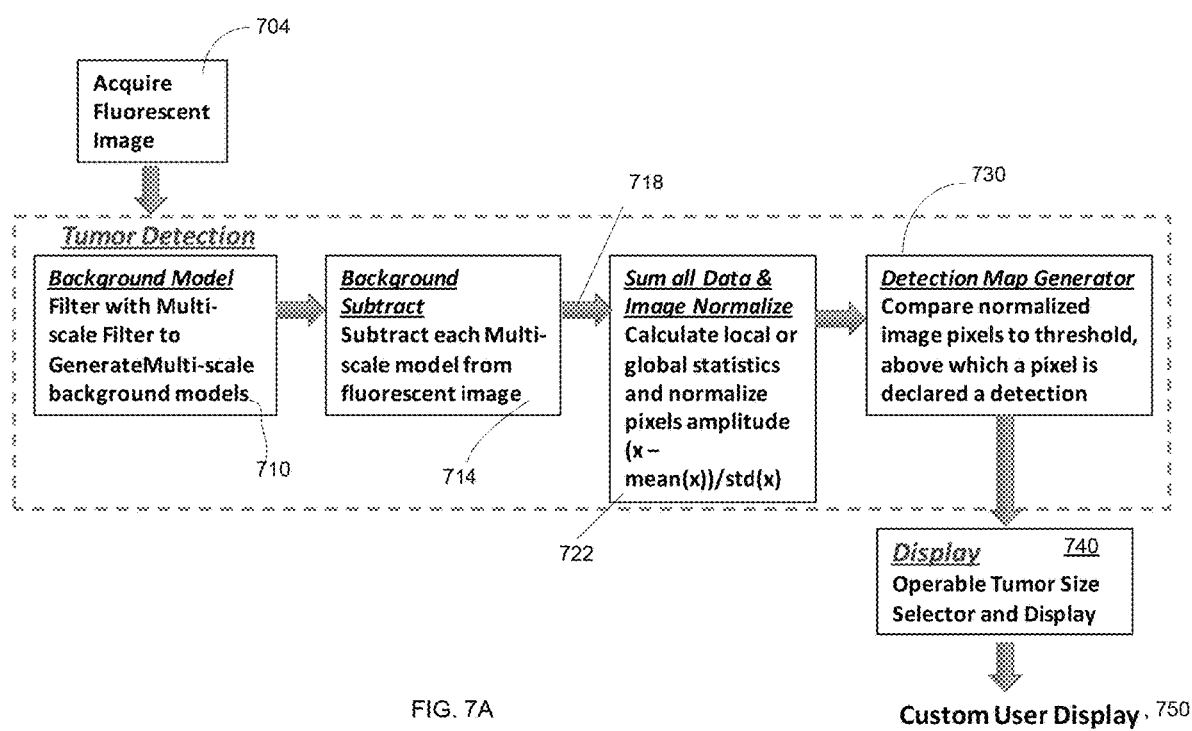
FIG. 7A is a flow-chart representing code for detecting targets of varying sizes and subsequent filtering to display targets of user-specified target size ranges as measured along the camera image plane at focus depth.

FIG. 7A illustrates schematically a flow-chart of the image processing process for a core product enabled by an embodiment of the intra-operative system 100 of FIG. 1. The components of the flow-diagram include a wavelet based multi-scale detection algorithm followed by morphological filtering and labeling of optical data to provide metrics on scale and shape of the components of the image. In particular, an input image frame 704, acquired at the wavelengths of input light 130 by the optical detection system 134, is processed at step 710 with the multi-scale wavelet detection algorithm, is subject to reduction of background signal (at step 714) to produce an image data output 718 with the amount of autofluorescence (created by endogenous fluorophores already present within normal tissue) is reduced. The imaging data 718 is further undergoing the normalization procedure, 722, and filtering defined by the user-formulated threshold of the target size, at step 730, to produce the output image frame 750 after the update of the user display at step 740.

It is understood that, in addition to producing the raw reflectance and fluorescence images of the object, additional real-time processing capabilities of an embodiment of the invention form a display of an additional optical output—a user identified "prioritized" tumors for resection indication, defined by setting the tumor size and/or morphology/delineation margins in the image output produced at step 730. The combination of algorithms tuned for this application provides useful information to the surgeon and generates real-time information that is advantageous in application in surgery. Up to-date, the related art has been silent with respect to such end-product in the context of intra-operative systems, which remains, therefore, novel.

In further reference to FIG. 7A, a related embodiment of the process of the invention can be optionally augmented with an additional pre-processing step (not shown), which involves a multi-frame non rigid-body registration and frame addition to increase the tumor SNR.

Figure 7B:
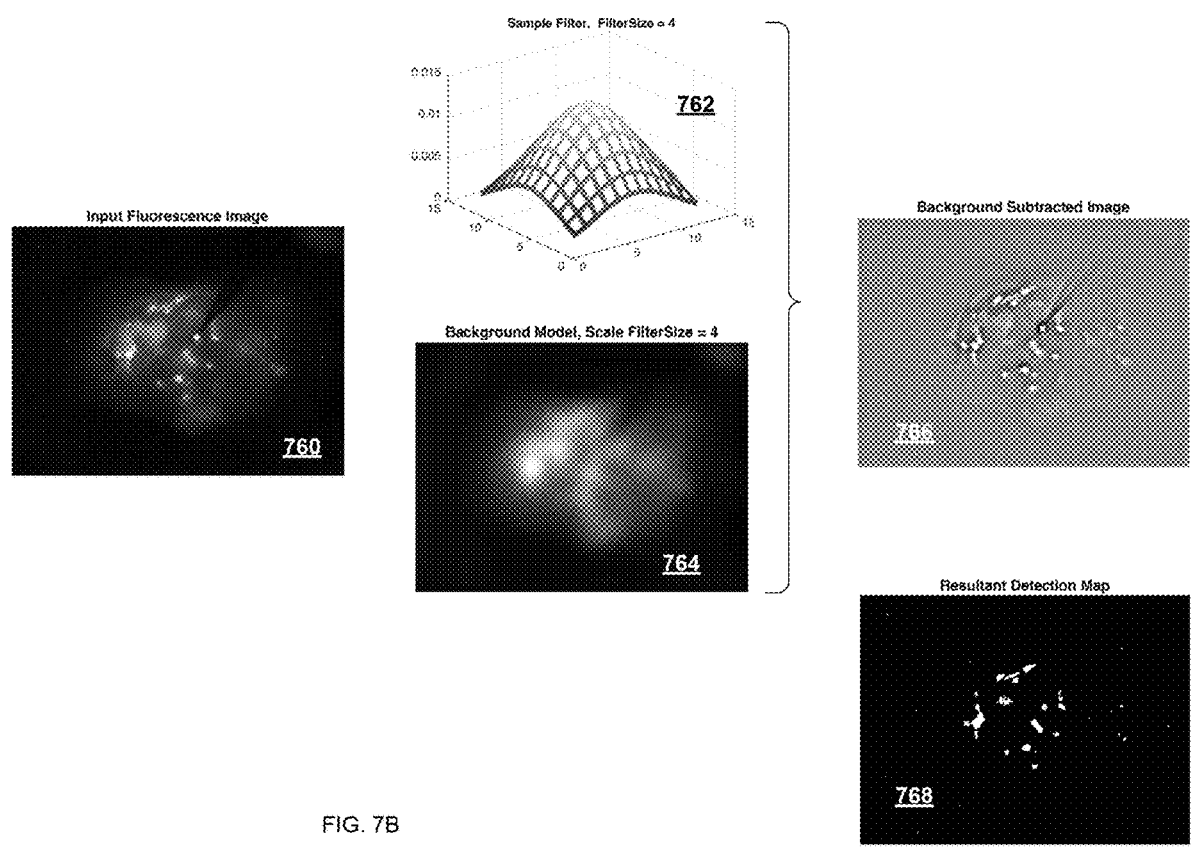
FIG. 7B shows a sample input fluorescence image and the resultant binary detection map from processing of data acquired with the use of the detection methodology of FIG. 9B

FIG. 7B illustrates an image 760 (acquired at step 704 of FIG. 7A); sample filter 762 and background model 764 used for target detection at step 714 of FIG. 7A; a background subtracted image 766 of step 714; and a resulting detection map of targets, procured from the comparison with the user-selected detection threshold of step 730 of FIG. 7A.

Figure 8A:
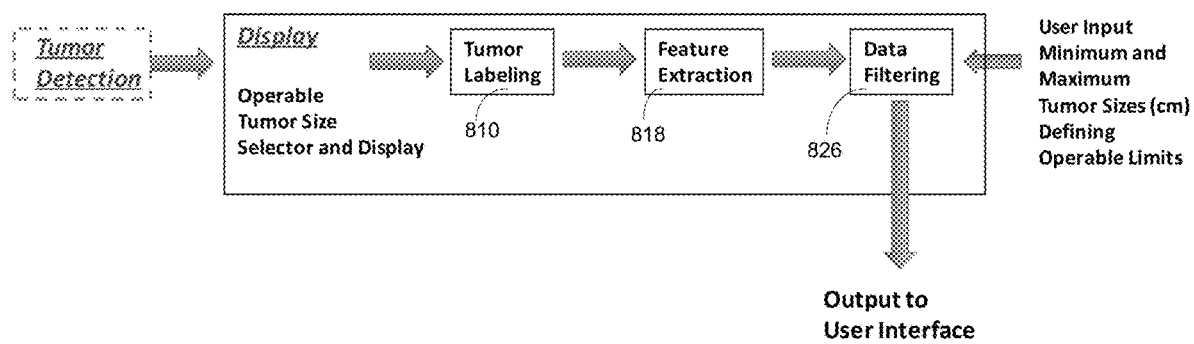
FIG. 8A is a flow chart representing code for classifying and displaying targets categorized by size.
Figure 8D:
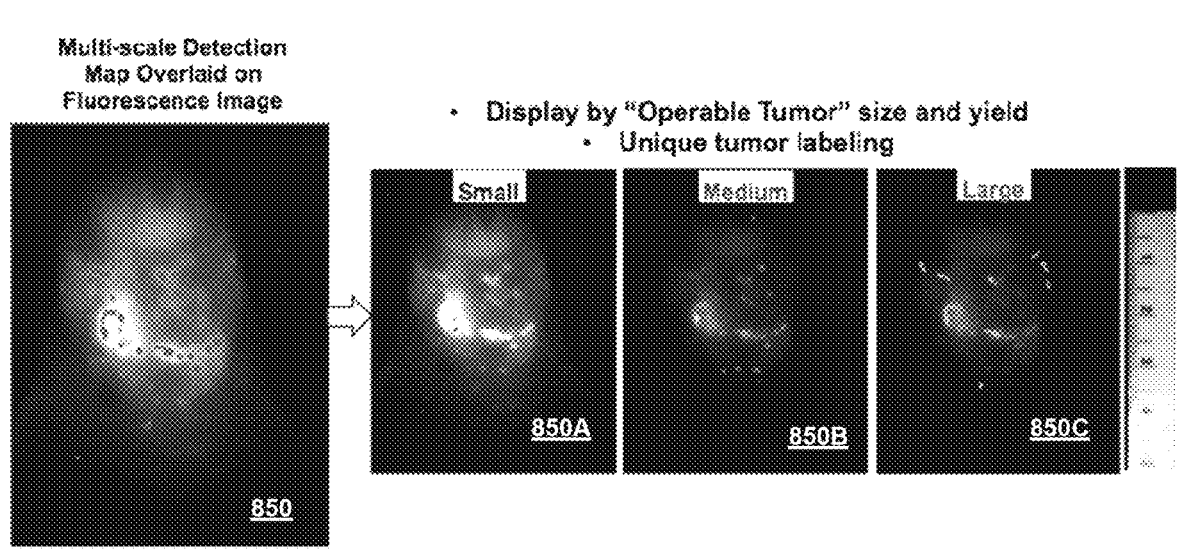

The output of the process of FIG. 7A (such as a target/tumor detection map 768, for example), is further used in the following display processing of step 740, described in FIG. 8A in more details as including a step of target labeling 810 (producing the image 814 of FIG. 8B); labeling of the detected target(s) with respect to their sizes at step 818 (producing the image 822 of FIG. 8B with a portion 822A thereof shown as a separate image); and a step of data filtering 826 (with the use of user-defined thresholds of target detection based on desired operable limits) that produces a map 830 of FIG. 8B, based on which the user interface receives separate images 840A, 840B, and 840C of targets quantified and grouped based on the targets' dimensions. FIG. 8D illustrates, in several image frames the multi-spatial-scale detection map of tumors in the biological tissue overlaid with the fluorescence image of the tissue (frame 850) and, separately "sized" subsets of small, medium, and large tumors presented in separate image frames 850A, 850B, 850C.

FIGS. 9A, 9B, and 9C provide code for implementation of the process of detection of targets, at the object, based on their dimensions (described in reference to FIGS. 7A, 7B, 8A, 8B, 8C, and 8D).

It is appreciated, therefore, that one of methods for imaging an object, disclosed in this application, includes (i) acquiring, with an optical imaging system that contains an optical detector having a spectral band of operation, first light and second fluorescent light from the object. The first light has a first wavelength, is generated by a first light source within the spectral band of operation, and is reflected by the object towards the optical detector. The first fluorescent light has a first fluorescent wavelength and is generated by a marker, contained at the object, in response to irradiation of the marker with light from a second light source. The first fluorescent wavelength defined within a second near-infrared (NIR-II) spectral region. The method further includes (ii) assessing a value equal to a difference between a first separation distance and a second separation distance, where the first separation distance represents a separation between a first portion of the object and the optical detector along an axis of the optical system, and the second separation distance represents a separation distance between a second portions of the object and the optical detector along the axis. The first portion of the object is associated with direct reflection of the first light, while the second portion of the object is associated with generation of the first fluorescent light and containing the marker. In one case, the marker includes a single-walled carbon nanotube, while the process of acquiring may include collecting the first light and the first fluorescent light through the optical imaging system along the same optical path. Alternatively or in addition, the step of acquiring, in the specific case, is devoid of mutual repositioning of the optical detector and the object. In one case, the first wavelength is defined within the NIR-II spectral band. In a particular implementation, the method may additionally includes the steps of (iii) irradiating the object with auxiliary light; (iv) acquiring, with the optical imaging system, third light from a third portion of the object (where the third portion is separated from the optical detector by a third distance along the axis, such that the second and third distances are not equal to one another, and where the third light includes fluorescence generated, at the first fluorescence wavelength, at the third portion of the object as a result of interaction of said second portion with the auxiliary light). In such particular implementation, the step of irradiating may be carried out with auxiliary light that is generated by the second source and/or at a different wavelength than that of the first light source. Furthermore, the step of acquiring may include collecting the first light and the first fluorescence light both of which have traversed the same optical elements of the optical system between the object and the optical detector, and be carried out with the optical detector that remains the only optical detector of the optical system.

Another method for imaging a specific object, disclosed in this application, includes (i) acquiring, with a single optical detector having spectral sensitivity in a NIR-II spectral band, radiation that has been emitted by the tissue in response to being irradiated with optical radiation delivered from at least first and second optical sources of a three-optical-source illumination system, in order to form optical data. The tissue contains a tissue portion tagged with a tissue-portion-selective biocompatible NIR-II fluorescent probe. The method further includes (ii) with a programmable processor operably connected with the single optical detector, determining first and second portions of the optical data (where the first portion of the optical data represents only a first radiation portion of the radiation that has been delivered from one of the first and second optical sources, while the second portion of the optical data represents only a second radiation portion of the radiation that has been delivered from another of the first and second optical sources). This version of a method further includes (iv) displaying, on a monitor of the system, the optical image of the tissue in which a visually-perceived difference between a first portion of the image and a second portion of the image is defined in response to a user input applied to the imaging system. Here, the first portion of the image is formed by the first radiation portion and the second portion of the image is formed by the second radiation portion. The process of imaging may include performing the steps of said acquiring, determining, and displaying in real time. The method may include, alternatively or in addition, a step of irradiating the tissue with radiation containing at least two of: visible light, light having a wavelength within a band of the spectral sensitivity, and light causing fluorescence of the fluorescent probe. In one implementation, the targeted tissue portion may be judiciously chosen to contain a sub-millimeter sized tumor, while the process of imaging includes causing actively targeted fluorescence in such tumor by irradiating the tumor with light from a third optical source of the illumination system. The user input may be applied to the imaging system to define a threshold size of the tissue portion to be displayed in the image. Alternatively or in addition, the user input may be applied to the imaging system to choose first and second depths in the tissue such as to define the first portion of the image as an image of a portion of tissue located at the first depth and the second portion of the image as an image of a portion of tissue located at the second depth.

A person of ordinary skill in the art will readily appreciate that the utility of the embodiments of the invention is quite broad, and includes, as non-limiting example, the operation in conjunction with endoscopic/laparoscopic probes, complementing the system and delivering imaging data from a cavity in the tissue of interest, a non-invasive transabdominal screening, as well as the system employing all-LED pumped version. In particular, To implement the idea of the invention for use in endoscopy or laparoscopy, the system of the invention is modified such as to deliver a first image, received from the optical data acquired at the distal end of a visible fiber-optic endoscope, to the NIR-II imager 134 with the use of the same coherent fiberoptic image bundle used for visible imagery. As an alternative, a custom-designed NIR optical system could be employed. Light at all of the present wavelengths can be transmitted through a standard silica-core optical fiber. The visible, in-band, and NIR-I band pump light sources could all be operationally coupled to the endoscope with the use of incoherent (non-imaging) fiberoptic light guides.

To implement this invention for non-invasive abdominal screening, a larger imaging lens with a longer working distance can be used, which lens is suitable for covering an approximately 1 ft×1 ft image field on the patient's body (abdomen, back, stomach, for example). Multiple redundant visible, in-band, and NIR-1 band pump source emitters equipped with optical diffusers (such as, for example, Edmund: #54-500) can be used to simplify the design, improve eye safety, and reduce system cost. Such source could be articulated using flexible ("gooseneck") guides and positioned so as to produce uniform illumination over the entire imaged field. To improve surface flatness of the tissue, an antireflection-coated "flattening" plate constructed from fused silica or low-fluorescing glass can be lightly pressed against the tissue surface to improve uniformity and maintain tighter focus within the visual field. Alternatively or in addition, since real-time operation is not important in this role, multiple image frames can be coherently added in the digital domain to improve the signal-to-noise ratio of the displayed imagery.

To implement this invention using eye-safe laser sources, one can use multiple low-power non-eyesafe lasers (laser diodes are one example) equipped with spatial and temporal coherence-spoiling diffusers specifically designed to force portions of the laser light to travel many different path lengths with a path length diversity exceeding the coherence length determined by that laser's spectral linewidth. Spatial and temporal coherence can both be reduced by random scattering within a three-dimensional bulk diffusing material (Teflon, silicone as examples) exhibiting sufficient path length diversity, as described above. For this purpose, lasers with a spectral linewidth of between 2 nm and 10 nm provide sufficient spectral purity to be easily filtered, yet have coherence lengths short enough to be decohered using cm-scale optical components.

To implement this invention using eye-safe LED pump sources, one can use multiple pump LEDs driven at low average current density (to reduce broadband thermal emission) and equipped by narrowband spectral filters with sufficient blocking characteristics extending out to wavelengths exceeding the spectral band edge of the imager 134 (approximately 2 um in one implementation). The in-band source 124 can remain spectrally unfiltered in this implementation, since it is intended to emit within the spectral bandpass of the imager 134.

The use of multiple discrete sources (those configured to generate visible light, NIR-I fluorescent pump light, and "in-band" light sources) does not preclude the use a single laser source that is spectrally agile (tunable) over, for example, the 700-1100 nm or wider range of wavelengths (i.e., a swept source, such as a Titanium Sapphire laser). Such use is intended to be within the scope of the invention, as an addition or alternative to simpler fixed-frequency sources such as laser diodes and LEDs. A spectrally agile source can enable a variation of the single-camera NIRF imaging methodology discussed above due to sweeping the narrow-spectral-band light-output (of a few nm wide) of a swept source across a contiguous wavelength range spanning the excitation ranges of various fluorophores as well as the in-band reflectance wavelengths. The optical detector in such embodiment is still configured to be sensitive to any fluorescence and/or reflectance signal returning from the irradiated object within the detector's acquisition spectral band. Some specific advantages of a single-camera-swept-laser-source implementation include:

(a) Enablement of "pump-side spectroscopy": A single spectral sweep can be performed slowly, by stepping the center wavelength of the optical output to discrete values during each of a sequence of multiple image frames: i) Distinguishing the presence and location of multiple fluorophores within the same object; ii) Determining the shift in excitation frequency of (as non-limiting examples: pH-sensitive, temperature-sensitive, chemically-sensitive) fluorophores in the object; iii) Determining the relative depth of fluorophore-containing targets on and/or within the object.

(b) Enablement of discrete source emulation: A repetitive spectral sweep can be performed quickly, with a wavelength cycle repeat time typically equal to one image frame time. During a single image frame time, the center wavelength can dwell at one or more specific frequencies to simulate the presence of one or more discrete source wavelengths (in-band sources, fluorescent pump sources) within that image frame time. The same wavelength sequence is then repeated during subsequent image frame times to i) emulate optical outputs at one or more fixed source wavelengths during an image frame; and ii) to provide the same functionality as a NIRF system using multiple fixed-frequency optical sources (exactly as previously discussed), but with the added ability to switch to a slow stepped or continuous spectral sweep over a number of image frames, as discussed above, at any time chosen by the user.

Notably, nothing stated above precludes the repetition of the entire sequences in time, along with techniques such as non-rigid body registration, to improve contrast or SNR. For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In specific cases, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. Other specific examples of the meaning of the terms "substantially", "about", and/or "approximately" as applied to different practical situations may have been provided elsewhere in this disclosure.

Embodiments of the invention have been described as including a processor controlled by instructions stored in a memory. The memory may be random access memory (RAM), read-only memory (ROM), flash memory or any other memory, or combination thereof, suitable for storing control software or other instructions and data. Some of the functions performed by the processor may have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. A fluorescence-based imaging system comprising:
an optical system including an optical train of components and an optical detection system that includes a single optical detector in optical communication with said optical train and separated from said optical train with an optical filter, the optical detection system having a spectral band of operation in an NIR-II spectral region, and
an illumination system that includes
a first light source configured to emit first light at a first wavelength within the spectral band of operation and
a second light source configured to emit second light at a second wavelength that is outside the spectral band of operation,
wherein the single optical detector is configured to form an image in imaging light characterized only by said spectral band of operation;
wherein said imaging light includes
only one first optical signal containing light received in direct reflection, of the first light emitted by the first light source, from an object and
only one second optical signal containing fluorescent light, said fluorescent light being at a third wavelength that is within the spectral band of operation, said fluorescent light having been generated by the object as a result of interaction of the object with the second light.

2. An imaging system according to claim 1, wherein the spectral band of operation is defined to include only the second near-infrared (NIR-II) spectral region.

3. An imaging system according to claim 1, wherein the illumination system is configured to emit the first and second lights simultaneously to cause the optical detection unit to generate simultaneously a first image at the first wavelength and a second image at the third wavelength.

4. An imaging system according to claim 1, further comprising
an auxiliary light source configured to emit visible light at a fourth wavelength that is outside of the spectral band of operation.

5. An imaging system according to claim 1, wherein the first and second light sources are configured to generate the first and second light in a time-multiplexed fashion.

6. An imaging system according to claim 1, wherein the first and second light sources are configured to operate simultaneously.

7. An imaging system according to claim 1, wherein the illumination system includes a single tuneable light source configured to generate the first and second lights.

8. An imaging system according to claim 1, wherein the illumination system is configured to operate with external user control.

9. An imaging system according to claim 1, wherein the third wavelength is a NIR wavelength in the spectral range from 1 micron to 1.8 microns.

10. A fluorescence-based imaging system comprising:
an optical system including an optical train of components and an optical detection system that includes a single optical detector in optical communication with said optical train and separated from said optical train with an optical filter the optical detection system having a spectral band of operation only in an NIR-II spectral region, and
an illumination system that includes
a first light source configured to emit first light at a first wavelength within the spectral band of operation and
a second light source configured to emit second light at a second wavelength that is outside the spectral band of operation,
wherein the single optical detector is configured to form an image in imaging light characterized only by said spectral band of operation;
wherein said imaging light includes
only one first optical signal containing light received in direct reflection of the first light, emitted by the first light source, from an object and
only one second optical signal containing fluorescent light, said fluorescent light being at a third wavelength that is within the spectral band of operation, said fluorescent light having been generated by the object as a result of interaction of the object with the second light.

11. An imaging system according to claim 10, wherein the first and second light sources are configured to generate the first and second light in a time-multiplexed fashion.

12. An imaging system according to claim 10, wherein the first and second light sources are configured to operate simultaneously.

13. An imaging system according to claim 10, wherein the first and second light sources are configured to operate by external user control.

14. An imaging system according to claim 10, further comprising
an auxiliary light source configured to emit visible light at a fourth wavelength that is outside of the spectral band of operation.

15. An imaging system according to claim 10,
wherein the illumination system is configured to emit the first and second lights simultaneously to cause the optical detection unit to generate simultaneously a first image at the first wavelength and a second image at the third wavelength.

16. An imaging system according to claim 10,
wherein the first and second wavelengths are defined such that, during imaging of a chosen object, the first light and the fluorescent light are received by the single optical detector along the same optical path through said optical train.

17. An imaging system according to claim 10, wherein the third wavelength is a NIR wavelength in the spectral range from 1 um to 1.8 um.

18. An imaging system according to claim 10,
wherein the spectral band of operation is defined within a spectral region spanning from 1 um to 1.8 um.

* * * * *